(12) United States Patent
Kakeya et al.

(10) Patent No.: US 8,772,297 B2
(45) Date of Patent: Jul. 8, 2014

(54) TGF-β SIGNAL TRANSDUCTION INHIBITOR

(75) Inventors: Hideaki Kakeya, Kyoto (JP); Akira Hattori, Kyoto (JP); Yasuaki Takasu, Kyoto (JP); Nobutaka Fujii, Kyoto (JP); Shinya Oishi, Kyoto (JP); Soichi Kojima, Saitama (JP); Mitsuko Hara, Saitama (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 13/579,843

(22) PCT Filed: Feb. 17, 2011

(86) PCT No.: PCT/JP2011/053428
§ 371 (c)(1),
(2), (4) Date: Nov. 5, 2012

(87) PCT Pub. No.: WO2011/102436
PCT Pub. Date: Aug. 25, 2011

(65) Prior Publication Data
US 2013/0045977 A1    Feb. 21, 2013

(30) Foreign Application Priority Data
Feb. 17, 2010    (JP) ................ 2010-032810

(51) Int. Cl.
*A61K 31/495*    (2006.01)
*C07D 295/104*    (2006.01)

(52) U.S. Cl.
CPC ............... *C07D 295/104* (2013.01)
USPC ............... 514/252.12; 546/226

(58) Field of Classification Search
CPC .............................. C07D 295/104
See application file for complete search history.

(56) References Cited

U.S. PATENT DOCUMENTS

2002/0151552 A1* 10/2002 Badwan ............ 514/252.12

OTHER PUBLICATIONS

Feytens, D., et al. "Highly Potent 4-Amino-indolo[2,3-c]azepin-3-one-Containing Somatostatin Mimetics with a Range of sst Receptor Selectivities." J. Med. Chem. (2009), vol. 52, pp. 95-104.*
American Chemical Society. STN. Chemical Abstract Service. RN CAS (Registry database).*
Halder, S.K., et al. "A Specific Inhibitor of TGF-β Receptor Kinase, SB-431542, as a Potent Antitumor Agent for Human Cancers." Neoplasia. (2005), vol. 7, No. 5, pp. 509-521.*
American Cancer Society. "Cancer Types." © 2013. Available from: < http://www.cancer.org/cancer/showallcancertypes/index >, pp. 1-2.*
Mayo Clinic. "Pancreatic Cancer." © 2012. Available from: < http://www.mayoclinic.com/health/pancreatic-cancer/DS00357/METHOD=print >.*
Mayo Clinic. © 2013. Available from: < http://www.mayoclinic.com/health/kidney-cancer/DS00360/METHOD=print&DSECTION=all >.*
Mayo Clinic. "Bladder cancer." © 2012. Available from: < http://www.mayoclinic.com/health/bladder-cancer/DS00177/METHOD=print&DSECTION=all >.*
Baade, P. "One in four cancers preventable—but first we need the willpower." The Conversation. Available from: < http://theconversation.com/one-in-four-cancers-preventable-but-first-we-need-the-willpower-5850 >, pp. 1-3.*
Mayo Clinic. "Cirrhosis." © 2013. Available from: < http://www.mayoclinic.com/health/cirrhosis/DS00373/METHOD=print&DSECTION=all >.*
American Chemical Society (ACS). STN CAS Registry Database. © 2013.*

* cited by examiner

*Primary Examiner* — Noble Jarrell
*Assistant Examiner* — John S Kenyon
(74) *Attorney, Agent, or Firm* — Leydig, Voit & Mayer, Ltd.

(57)    ABSTRACT

The present invention provides a compound represented by the following formula (I) or a physiologically acceptable salt thereof, and use thereof for the prophylaxis or treatment of TGF-β-related diseases:

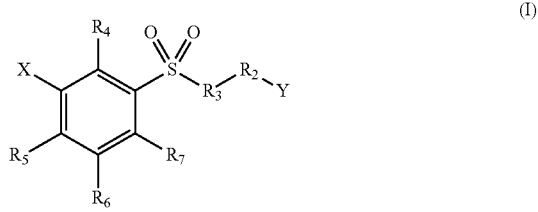

wherein
Y is a hydrogen atom and the like;
$R_2$ is

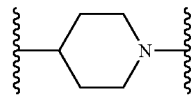

and the like;
$R_3$ is —$NR_8$—$R_9$— and the like;
$R_4$, $R_5$, $R_6$ and $R_7$ are the same or different and each is a hydrogen atom and the like; and
X is

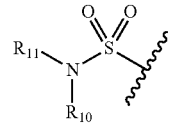

and the like.

18 Claims, 3 Drawing Sheets

… (1)

TGF-β SIGNAL TRANSDUCTION INHIBITOR

CROSS-REFERENCE TO RELATED APPLICATIONS

This patent application is the U.S. national phase of PCT/JP2011/053428, filed on Feb. 17, 2011, which claims the benefit of Japanese Patent Application No. 2010-032810, filed on Feb. 17, 2010, which are incorporated by reference in their entireties herein.

TECHNICAL FIELD

The present invention relates to a novel compound that inhibits TGF-β signal transduction and use thereof.

BACKGROUND ART

Transforming Growth Factor (TGF)-β is a cytokine involved in various physiological phenomena such as acceleration or suppression of cell growth, cell differentiation, development and the like. Pathologically, moreover, it is known to cause diseases closely related to the fibrillization of organ, such as cancer, cirrhosis, renal failure (glomerulonephritis), arteriosclerosis, rheumatoid arthritis and the like (non-patent document 1).

TGF-β forms TGF-β superfamily together with bone morphogenetic factors, activin and the like, since they show homology in the constituent amino acid. The members of the TGF-β superfamily are all synthesized as precursors, after which pre-form and then pro-form sequences are eliminated by protease, whereby a mature protein with a molecular weight of about 12 kDa is formed. Since two such monomers form a covalent bond by disulfide bridging, a dimer with a molecular weight of about 25 kDa is formed (non-patent document 2).

Human TGF-β includes three kinds of isoforms (TGF-β1, TGF-β2 and TGF-β3), which are expressed in a tissue specific manner (non-patent document 2). The signal of each TGF-β isoform is transmitted via a signal transduction pathway, and exerts each physiological action. That is, when TGF-β is bound to a type II TGF-β receptor, which is a receptor-like serine/threonine kinase, a receptor complex consisting of two molecules of type II receptor and two molecules of type I TGF-β receptor/Alk-5 is formed, and type II receptor phosphorylates a serine residue of type I TGF-β receptor/Alk-5 and activates it. Type I TGF-β receptor/Alk-5 is also a serine/threonine kinase, like type II receptor, and activated type I receptor/Alk-5 phosphorylates a serine residue of Smad2 or Smad3, which is a transcription factor present in the cytoplasm. The phosphorylated Smad2 or Smad3 forms a complex with Smad4 in the cytoplasm, are thereafter transferred to the nucleus, bound to a target sequence called CAGA box present in a promoter region of a collagen gene which is a target gene deeply involved in the fibrillization, and induce transcription expression together with a co-activator (non-patent documents 1, 3, 4).

As a means to improve pathology caused by the action of TGF-β, attempts have been made to inhibit binding of TGF-β and a receptor by a neutralization antibody, a soluble receptor or a low-molecular-weight compound, inhibit the kinase activity of a receptor, which is caused by binding of TGF-β, with a low-molecular-weight compound and the like. However, the development of a novel TGF-β signal transduction inhibitor has been desired (non-patent document 5).

On the other hand, non-patent document 6 discloses N-substituted piperidinyl-diphenylsulfonyl-sulfoneamides that inhibit secreted Frezzled-Related Protein I (sFRP-1) and control Wnt signaling (non-patent document 6).

DOCUMENT LIST

Non-Patent Documents non-patent document 1: Heldin C. H. et al. (1997) Nature, 390, 465-471
non-patent document 2: Massague J. (1998) Annu. Rev. Biochem., 67, 735-791
non-patent document 3: Shi Y. and Massague J. (2003) Cell, 113,
non-patent document 4: Dennler S. et al. (1998) EMBO J., 17, 3091-3100
non-patent document 5: Yingling et al. (2004) Nat. Rev. Drug Discov., 3, 1011-1022
non-patent document 6: William J. Moore et al. (2009) J. Med. Chem., 52, 105-116

SUMMARY OF THE INVENTION

Problems to be Solved by the Invention

Provision of a compound that inhibits TGF-β signal transduction, as well as a TGF-β inhibitor utilizing the compound and an agent for the prophylaxis or treatment of a TGF-β-related disease.

Means of Solving the Problems

In an attempt to solve the aforementioned problems, the present inventors have established a highly sensitive cell line for screening for a compound that inhibits TGF-β signal transduction, performed high-throughput screening and conducted intensive studies. As a result, they have found that a compound represented by the formula (I) unexpectedly has a superior TGF-β signal transduction inhibitory activity based on its specific chemical structure and can be a medicament useful as a prophylactic or therapeutic drug for a TGF-β-related disease in mammals, and completed the present invention based on these findings.

Accordingly, the present invention relates to the following:
[1] A compound represented by the following formula (I):

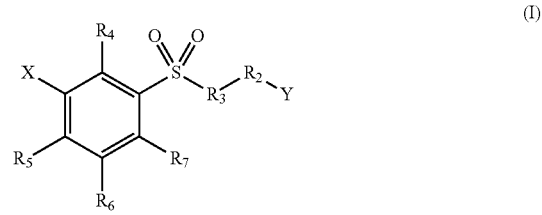

wherein
Y is a hydrogen atom, a carboxyl group or

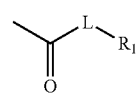

(wherein L is an oxygen atom or a bond, and $R_1$ is optionally substituted $C_{1-6}$ alkyl);

$R_2$ is

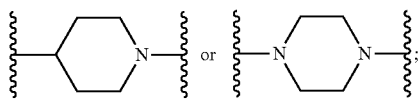

$R_3$ is —$NR_8$—$R_9$— or a bond (wherein $R_8$ is a hydrogen atom or $C_{1-6}$ alkyl, and $R_9$ is $C_{1-6}$ alkylene);
$R_4$, $R_5$, $R_6$ and $R_7$ are the same or different and each is a hydrogen atom or $C_{1-6}$ alkyl; and
X is

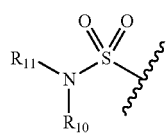

or a hydrogen atom (wherein $R_{10}$ is a hydrogen atom or $C_{1-6}$ alkyl; and
$R_{11}$ is optionally substituted phenyl, optionally substituted $C_{1-6}$ alkyl or a hydrogen atom, or
$R_{10}$ and $R_{11}$ form, together with the nitrogen atom bonded thereto, an optionally substituted 5- to 7-membered cyclic amino group, or a physiologically acceptable salt thereof.
The compound or a physiologically acceptable salt thereof of [1], wherein Y is

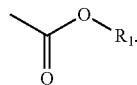

[3] The compound or a physiologically acceptable salt thereof of [1] or [2], wherein $R_{11}$ is a group represented by the following formula:

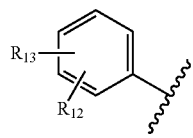

wherein
$R_{12}$ is a hydrogen atom, furyl or thienyl; and
$R_{13}$ is optionally substituted amino, optionally substituted $C_{1-6}$ alkyl, hydroxy, optionally substituted $C_{1-6}$ alkoxy, $C_{1-6}$ alkanoyl, $C_{6-10}$ aroyl or $N_3$.
[4] The compound or a physiologically acceptable salt thereof of [3], wherein $R_{13}$ is an amino group optionally mono- or di-substituted by $C_{1-6}$ alkyl or $C_{1-6}$ alkanoyl, or an optionally substituted 5- to 7-membered cyclic amino group.
[5] The compound or a physiologically acceptable salt thereof of [2], which is
4-[3-(piperidine-1-sulfonyl)benzenesulfonyl]piperazine-1-carboxylic acid tert-butyl ester (Y043),
4-{[3-(piperidine-1-sulfonyl)benzenesulfonylamino]-methyl}-piperidine-1-carboxylic acid benzyl ester (Y053),
4-({methyl-[3-(methyl-p-tolylsulfamoyl)benzenesulfonyl]amino}methyl)piperidine-1-carboxylic acid tert-butyl ester (Y191),
4-[({3-[(4-tert-butylphenyl)methylsulfamoyl]benzenesulfonyl}methylamino)-methyl]piperidine-1-carboxylic acid tert-butyl ester (Y205),
4-{[3-(4-tert-butylphenylsulfamoyl)-2,4,5,6-tetramethyl-benzenesulfonylamino]methyl}piperidine-1-carboxylic acid tert-butyl ester (Y335),
4-{[3-(piperidine-1-sulfonyl)benzenesulfonylamino] methyl}piperidine-1-carboxylic acid tert-butyl ester (Y029),
4-[(3-diethylsulfamoylbenzenesulfonylamino)methyl]piperidine-1-carboxylic acid tert-butyl ester (Y080),
4-{[3-(morpholine-4-sulfonyl)benzenesulfonylamino] methyl}piperidine-1-carboxylic acid tert-butyl ester (Y081),
4-[(3-sulfamoylbenzenesulfonylamino)methyl]piperidine-1-carboxylic acid tert-butyl ester (Y082),
4-(benzenesulfonylaminomethyl)piperidine-1-carboxylic acid tert-butyl ester (Y083),
4-{[3-(cyclohexylmethylsulfamoyl)benzenesulfonylamino] methyl}-piperidine-1-carboxylic acid tert-butyl ester (Y101),
4-[(3-phenylsulfamoylbenzenesulfonylamino)methyl]piperidine-1-carboxylic acid tert-butyl ester (Y098),
4-{[3-(4-methoxyphenylsulfamoyl)benzenesulfonylamino] methyl}piperidine-1-carboxylic acid tert-butyl ester (Y141),
4-{[3-(3-methoxyphenylsulfamoyl)benzenesulfonylamino] methyl}piperidine-1-carboxylic acid tert-butyl ester (Y142),
4-{[3-(2-methoxyphenylsulfamoyl)benzenesulfonylamino] methyl}piperidine 1-carboxylic acid tert-butyl ester (Y140),
4-{[3-(4-trifluoromethylphenylsulfamoyl)benzenesulfonylamino]methyl}-piperidine-1-carboxylic acid tert-butyl ester (Y145),
4-{[3-(2-acetylaminophenylsulfamoyl)benzenesulfonylamino]methyl}-piperidine-1-carboxylic acid tert-butyl ester (Y147),
4-[(3-p-tolylsulfamoylbenzenesulfonylamino)methyl]piperidine-1-carboxylic acid tert-butyl ester (Y155),
4-{[3-(4-tert-butylphenylsulfamoyl)benzenesulfonylamino] methyl}piperidine-1-carboxylic acid tert-butyl ester (Y177),
4-{[3-(4-piperidin-1-yl-phenylsulfamoyl)benzenesulfonylamino]methyl}piperidine-1-carboxylic acid tert-butyl ester (Y224),
4-{[3-(4-diethylaminophenylsulfamoyl)benzenesulfonylamino]methyl}-piperidine-1-carboxylic acid tert-butyl ester (Y186),
4-{[3-(4-dimethylaminophenylsulfamoyl)benzenesulfonylamino]methyl}-piperidine-1-carboxylic acid tert-butyl ester (Y178),
4-{[3-(4-morpholin-4-yl-phenylsulfamoyl)benzenesulfonylamino]methyl}piperidine-1-carboxylic acid tert-butyl ester (Y185),
4-{[3-(4-acetylphenylsulfamoyl)benzenesulfonylamino] methyl}piperidine-1-carboxylic acid tert-butyl ester (Y192),
4-({3-[4-(1-hydroxyethyl)phenylsulfamoyl] benzenesulfonylamino}methyl)-piperidine-1-carboxylic acid tert-butyl ester (Y195),
4-{[3-(4-hydroxyphenylsulfamoyl)benzenesulfonylamino] methyl}piperidine 1-carboxylic acid tert-butyl ester (Y196),
4-{[3-(4-oxanylmethoxyphenylsulfamoyl)benzenesulfonylamino]methyl}-piperidine-1-carboxylic acid tert-butyl ester (Y198), 4-{[3-(4-azidophenylsulfamoyl)benzenesulfonylamino]
methyl}piperidine-1-carboxylic acid tert-butyl ester
(Y241),
4-(4-{3-[(1-tert-butoxycarbonylpiperidin-4-ylmethyl)sulfa-
moyl]benzenesulfonylamino}phenyl)piperazine-1-car-
boxylic acid tert-butyl ester (Y260),
4-({3-[4-(4-benzoylpiperazin-1-yl)phenylsulfamoyl]
benzenesulfonylamino}methyl)piperidine-1-carboxylic
acid tert-butyl ester (Y366),
4-{[3-(4-dimethylamino-3-furan-2-yl-phenylsulfamoyl)
benzenesulfonylamino]methyl}piperidine-1-carboxylic
acid tert-butyl ester (Y244),
4-{[3-(3-furan-2-yl-4-piperidin-1-yl-phenylsulfamoyl)ben-
zenesulfonylamino]methyl}piperidine-1-carboxylic acid
tert-butyl ester (Y250),
4-{[3-(3-furan-2-yl-phenylsulfamoyl)benzenesulfony-
lamino]methyl}piperidine-1-carboxylic acid tert-butyl
ester (Y284),
4-{[3-(3-thiophen-2-yl-phenylsulfamoyl)benzenesulfony-
lamino]methyl}piperidine-1-carboxylic acid tert-butyl
ester (Y296),
or a physiologically acceptable salt thereof,
[6] The compound or a physiologically acceptable salt thereof
of [1], which is 4-{[3-(4-dimethylamino-3-furan-2-yl-phe-
nylsulfamoyl)benzenesulfonylamino]methyl}piperidine
(Y516), 4-{[3-(4-dimethylamino-3-furan-2-yl-phenylsulfa-
moyl)benzenesulfonylamino]methyl}-1-butyryl-piperidine
(Y639) or a physiologically acceptable salt thereof.
[7] A pharmaceutical composition comprising the compound
or a physiologically acceptable salt thereof of [1] or [2].
[8] A TGF-β signal transduction inhibitor comprising the
compound or a physiologically acceptable salt thereof of [1]
or [2].
[9] A prophylactic or therapeutic agent for a TGF-β-related
disease, comprising the compound or a physiologically
acceptable salt thereof of [1] or [2].
[10] The prophylactic or therapeutic agent of [9], wherein the
TGF-β-related disease is a sclerotic disease or cancer associ-
ated with tissue fibrillization.
[11] The compound or a physiologically acceptable salt
thereof of [1] or [2] for use in the prophylaxis or treatment of
a TGF-β-related disease.
[12] The compound or a physiologically acceptable salt
thereof of [11], wherein the TGF-β-related disease is a scle-
rotic disease or cancer associated with tissue fibrillization.
[13] A method for the prophylaxis or treatment of a TGF-β-
related disease in a mammal, comprising administering a
prophylactically or therapeutically effective amount of the
compound or a physiologically acceptable salt thereof of [1]
or [2] to said mammal.
[14] The method of [13], wherein the TGF-β-related disease
is a sclerotic disease or cancer associated with tissue fibrilli-
zation.

Effect of the Invention

Since the compound of the present invention effectively
inhibits TGF-β signal transduction, it is useful as a prophy-
lactic or therapeutic drug for a TGF-β-related disease.

DESCRIPTION OF EMBODIMENTS

Figure 1:
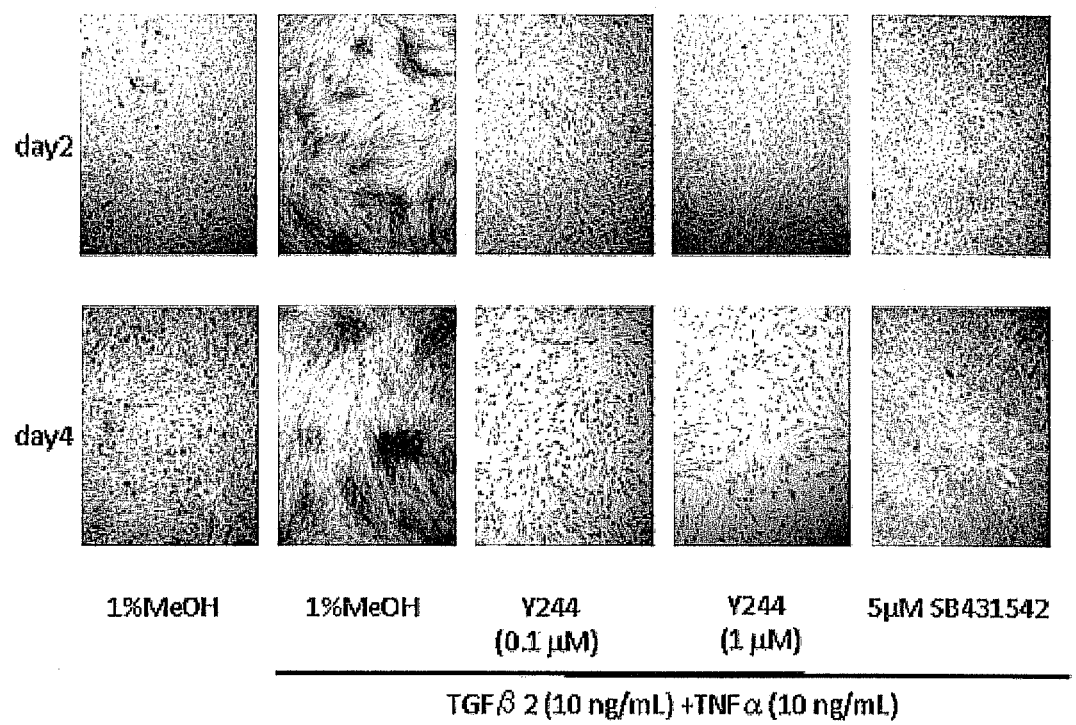
FIG. 1 shows the effect of Y244 on EMT, which is induced
by TGF-β.

The terms in the present specification are explained below.
In the formula (I), Y is preferably a hydrogen atom or

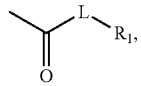

more preferably,

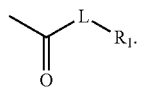

L is an oxygen atom or a bond, more preferably an oxygen
atom.
Therefore, in a preferable embodiment, Y is

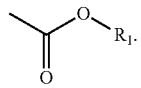

In the formula (I), the "$C_{1-6}$ alkyl" in the "optionally sub-
stituted $C_{1-6}$ alkyl" for $R_1$ means linear or branched alkyl
having 1-6 carbon atoms. Specific examples include methyl,
ethyl, propyl, isopropyl, butyl, isobutyl, sec-butyl, tert-butyl,
pentyl, isopentyl, hexyl and the like. The "$C_{1-6}$" means that
the number of carbon atom is 1-6.
The $C_{1-6}$ alkyl for $R_1$ is preferably methyl, ethyl, propyl,
isopropyl, butyl, isobutyl, sec-butyl, tert-butyl and the like,
more preferably methyl, tert-butyl and the like.
The $C_{1-6}$ alkyl for $R_L$ may have 1 to 3, preferably 1 or 2,
substituent(s) at substitutable position(s). Examples of such
substituent include $C_{6-14}$ aryl, a halogen atom, $C_{3-8}$
cycloalkyl, $C_{2-7}$ oxacycloalkyl, optionally esterified carboxy,
nitro, amino, hydroxy, thiol and the like.
As $C_{6-14}$ aryl, phenyl, naphthyl, anthryl, phenanthryl and
the like can be mentioned. Of these, phenyl and the like are
preferable.
As the "halogen atom", fluorine, chlorine, bromine and
iodine can be mentioned. Of these, fluorine and chlorine are
preferable.
As the $C_{3-8}$ cycloalkyl, cyclopropyl, cyclobutyl, cyclopen-
tyl, cyclohexyl, cycloheptyl, cyclooctyl and the like can be
mentioned.
As the $C_{2-7}$ oxacycloalkyl, epoxy, 2-oxetanyl, 2-tetrahy-
drofuranyl, 3-tetrahydrofuranyl, 2-tetrahydropyranyl, 3-tet-
rahydropyranyl, 4-tetrahydropyranyl and the like can be men-
tioned.
Examples of the esterified carboxy in the optionally esteri-
fied carboxy include an alkoxycarbonyl group having a car-
bon number of 2 to 5 (e.g., methoxycarbonyl, ethoxycarbo-
nyl, propoxycarbonyl, butoxycarbonyl, tert-butoxycarbonyl
and the like), an aralkyloxycarbonyl group having a carbon number of 8 to 10 (e.g., benzyloxycarbonyl and the like), an aryloxycarbonyl group having a carbon number of 7 to 15 (e.g., phenoxycarbonyl, p-tolyloxycarbonyl and the like) optionally substituted by 1 or 2 alkyl groups having a carbon number of 1 to 3, and the like.

In the "optionally substituted $C_{1-6}$ alkyl" for $R_1$, the substituent of the substituted $C_{1-6}$ alkyl is preferably $C_{6-14}$ aryl and the like, more preferably phenyl and the like.

$R_1$ is particularly preferably tert-butyl or benzyl.

$R_2$ is preferably

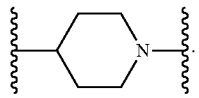

$R_3$ is preferably —$NR_8$—$R_9$—.

As the "$C_{1-6}$ alkyl" for $R_8$, those exemplified as the aforementioned $R_1$ can be mentioned. The $C_{1-6}$ alkyl for $R_8$ is preferably methyl, ethyl, propyl and the like, more preferably methyl and the like.

$R_8$ is preferably a hydrogen atom, methyl and the like, most preferably a hydrogen atom and the like.

As the "$C_{1-6}$ alkylene" for $R_9$, —$CH_2$—, —$(CH_2)_2$—, —$(CH_2)_3$—, —$(CH_2)_4$—, —$(CH_2)_6$—, —$(CH(CH_3))$—, —$C(CH_3)_2$—, —$(CH(CH_3))_2$—, —$(CH_2)_2C(CH_3)_2$—, —$(CH_2)_3C(CH_3)_2$— and the like can be mentioned. $R_9$ is preferably —$CH_2$—, —$(CH_2)_2$—, —$(CH_2)_3$—, —$(CH_2)_4$— and the like, more preferably —$CH_2$— and the like.

When $R_2$ is

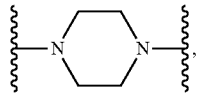

$R_3$ is preferably a bond.

As the "$C_{1-6}$ alkyl" for $R_4$, $R_5$, $R_6$ or $R_7$, those exemplified as the aforementioned $R_1$ can be mentioned. The $C_{1-6}$ alkyl for $R_4$, $R_5$, $R_6$ or $R_7$ is preferably methyl, ethyl, propyl and the like, more preferably methyl and the like.

$R_4$, $R_5$, $R_6$ and $R_7$ are preferably the same group. All of $R_4$, $R_5$, $R_6$ and $R_7$ are preferably hydrogen atoms or methyl, more preferably hydrogen atoms.

X is preferably

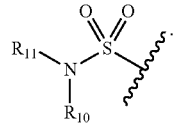

As the "$C_{1-6}$ alkyl" for $R_{10}$, those exemplified as the aforementioned $R_1$ can be mentioned. The $C_{1-6}$ alkyl for $R_{10}$ is preferably methyl, ethyl, propyl and the like, more preferably methyl, ethyl and the like.

$R_{10}$ is preferably a hydrogen atom, methyl, ethyl and the like, more preferably a hydrogen atom.

As the "$C_{1-6}$ alkyl" of the "optionally substituted $C_{1-6}$ alkyl" for $R_{11}$, those exemplified as the aforementioned $R_1$ can be mentioned. The $C_{1-6}$ alkyl for $R_{11}$ is preferably methyl, ethyl, propyl and the like, more preferably methyl and the like.

The $C_{1-6}$ alkyl for $R_{11}$ optionally has 1 to 3, preferably 1 or 2, substituent(s) at substitutable position(s). As such substituent, those exemplified as the substituents for the aforementioned "substituted $C_{1-6}$ alkyl" for $R_1$ can be mentioned.

In the "optionally substituted $C_{1-6}$ alkyl" for $R_{11}$, the substituent of the substituted $C_{1-6}$ alkyl is preferably $C_{3-8}$ cycloalkyl and the like, more preferably cyclohexyl and the like.

The phenyl for $R_{11}$ optionally has 1 to 3, preferably 1 or 2, substituent(s) at substitutable position(s). As such substituent, "optionally substituted amino", "optionally substituted $C_{1-6}$ alkyl", "optionally substituted $C_{1-6}$ alkoxy", $C_{1-6}$ alkanoyl, $C_{6-10}$ aroyl, $C_{3-8}$ cycloalkyl, a halogen atom, $N_3$, furyl, thienyl, nitro, hydroxy, thiol, carboxy and the like can be mentioned.

Examples of the "optionally substituted amino" which is the substituent that phenyl for $R_{11}$ optionally has include amino optionally mono- or di-substituted by $C_{1-6}$ alkyl, $C_{2-6}$ alkenyl, $C_{3-8}$ cycloalkyl, $C_{3-8}$ cycloalkenyl, $C_{6-14}$ aryl, $C_{1-6}$ alkanoyl, $C_{6-10}$ aroyl etc., and optionally substituted 5- to 7-membered cyclic amino.

Examples of the $C_{1-6}$ alkyl include those exemplified as the aforementioned $R_1$. The $C_{1-6}$ alkyl is preferably methyl, ethyl, propyl, isopropyl, butyl, isobutyl, sec-butyl, tert-butyl and the like, more preferably methyl, ethyl, tert-butyl and the like.

Examples of the $C_{2-6}$ alkenyl include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like.

As the $C_{3-8}$ cycloalkyl, those exemplified as the substituent of the aforementioned $C_{1-6}$ alkyl for $R_1$ can be mentioned.

As the $C_{3-8}$ cycloalkenyl, 2-cyclopenten-1-yl, 3-cyclopenten-1-yl, 2-cyclohexen-1-yl, 3-cyclohexen-1-yl and the like can be mentioned.

As the $C_{6-14}$ aryl, those exemplified as the substituent of the aforementioned $C_{1-6}$ alkyl for $R_1$ can be mentioned.

As the $C_{1-6}$ alkanoyl, formyl, acetyl, propionyl, butyryl, isobutyryl, pivaloyl and the like can be mentioned. The $C_{1-6}$ alkanoyl is preferably formyl, acetyl or propionyl, more preferably acetyl.

As the $C_{6-10}$ aroyl, benzoyl, naphthoyl and the like can be mentioned. The $C_{6-10}$ aroyl is preferably benzoyl.

As the "5- to 7-membered cyclic amino group" of the "optionally substituted 5- to 7-membered cyclic amino group", a 5- to 7-membered cyclic amino group containing, as a ring constituting atom besides carbon atom, at least one nitrogen atom, and optionally further containing 1 or 2 hetero atoms selected from an oxygen atom, a sulfur atom and a nitrogen atom can be mentioned. Preferable examples of the cyclic amino group include 1-pyrrolidinyl, 1-imidazolidinyl, 1-pyrazolidinyl, 1-piperidinyl, 1-piperazinyl, morpholino, is thiomorpholino, 3-thiazolidinyl, 3-oxazolidinyl and the like. The cyclic amino group is more preferably 1-pyrrolidinyl, 1-piperidinyl, 1-piperazinyl, morpholino and the like, further preferably 1-piperidinyl, 1-piperazinyl, morpholino and the like.

The "5- to 7-membered cyclic amino group" optionally has 1 to 3 (preferably 1 or 2) substituent(s) at substitutable position(s). As the substituent, those exemplified as the substituents for the aforementioned "substituted $C_{1-6}$ alkyl" for $R_1$ can be mentioned.

The substituent of the "substituted 5- to 7-membered cyclic amino group" is preferably optionally esterified carboxy and the like, more preferably carboxy, alkoxycarbonyl having a carbon number of 2 to 5 and the like.

The "optionally substituted amino" is preferably amino optionally mono- or di-substituted by $C_{1-6}$ alkyl or $C_{1-6}$ alkanoyl, or optionally substituted 5- to 7-membered cyclic amino.

Preferable examples of the substituted amino group include methylamino, dimethylamino, ethylamino, diethylamino, propylamino, dibutylamino, tert-butylamino, diallylamino, cyclohexylamino, acetylamino, propionylamino, benzoylamino, phenylamino, N-methyl-N-phenylamino, 1-piperidinyl, 1-piperazinyl, morpholino and the like.

As the "$C_{1-6}$ alkyl" of the "optionally substituted $C_{1-6}$ alkyl", which is the substituent that phenyl for $R_{11}$ optionally has, those exemplified as the aforementioned $R_1$ can be mentioned. The $C_{1-6}$ alkyl is preferably methyl, ethyl, propyl, isopropyl, butyl, isobutyl, sec-butyl, tert-butyl and the like, more preferably methyl, ethyl, tert-butyl and the like.

The $C_{1-6}$ alkyl optionally has 1 to 3 substituents at substitutable position(s). As such substituent, those exemplified as the substituents for the aforementioned "substituted $C_{1-6}$ alkyl" for $R_1$ can be mentioned. The substituent is preferably a halogen atom (e.g., fluorine atom, chlorine atom), hydroxy and the like.

As the "$C_{1-6}$ alkoxy" of the "optionally substituted $C_{1-6}$ alkoxy", which is the substituent that phenyl for $R_{11}$ optionally has, methoxy, ethoxy, propoxy, isopropoxy, butoxy, isobutoxy, sec-butoxy, tert-butoxy, pentyloxy, isopentyloxy, neopentyloxy, hexyloxy and the like can be mentioned. The $C_{1-6}$ alkoxy is preferably methoxy, ethoxy, propoxy, isopropoxy and the like, more preferably methoxy, ethoxy and the like.

The $C_{1-6}$ alkoxy optionally has 1 to 3 substituents at substitutable position(s). As such substituent, those exemplified as the substituents for the aforementioned "substituted $C_{1-6}$ alkyl" for $R_1$ can be mentioned. The substituent is preferably $C_{2-7}$ oxacycloalkyl (e.g., epoxy, 2-tetrahydrofuranyl).

As the "$C_{1-6}$ alkanoyl", which is the substituent that phenyl for $R_{11}$ optionally has, formyl, acetyl, propionyl, butyryl, isobutyryl, pivaloyl and the like can be mentioned. The $C_{1-6}$ alkanoyl is preferably formyl, acetyl, propionyl and the like, more preferably acetyl and the like.

As the "$C_{1-6}$ aroyl", which is the substituent that phenyl for $R_{11}$ optionally has, benzoyl, naphthoyl and the like can be mentioned. The $C_{6-10}$ aroyl is preferably benzoyl.

As the "$C_{3-8}$ cycloalkyl", which is the substituent that phenyl for $R_{11}$ optionally has, those exemplified as the substituents for the aforementioned "substituted $C_{1-6}$ alkyl" for $R_1$ can be mentioned. The $C_{3-8}$ cycloalkyl is preferably cyclohexyl.

As the "halogen atom", which is the substituent that phenyl for $R_{11}$ optionally has, those exemplified as the substituents for the aforementioned "substituted $C_{1-6}$ alkyl" for $R_1$ can be mentioned.

The "furyl", which is the substituent that phenyl for $R_{11}$ optionally has, includes 2-furyl and 3-furyl, preferably 2-furyl.

The "thienyl", which is the substituent that phenyl for $R_{11}$ optionally has, includes 2-thienyl and 3-thienyl, preferably 3-thienyl.

The "optionally substituted phenyl" for $R_{11}$ is preferably a group represented by the following formula:

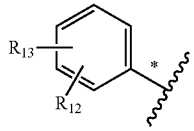

wherein
$R_{12}$ is a hydrogen atom, furyl or thienyl; and
$R_{13}$ is an optionally substituted amino, optionally substituted $C_{1-6}$ alkyl, hydroxy, optionally substituted $C_{1-6}$ alkoxy, $C_{1-6}$ alkanoyl, $C_{6-10}$ aroyl or $N_3$.

Here, the definition of each of "furyl", "thienyl", "optionally substituted amino", "optionally substituted $C_{1-6}$ alkyl", "optionally substituted $C_{1-6}$ alkoxy", "$C_{1-6}$ alkanoyl" and "$C_{6-10}$ aroyl" is the same as that of the substituent of the aforementioned "substituted phenyl" for $R_{11}$.

While $R_{12}$ on the phenyl group may be in any configuration of ortho, meta and para relative to the substituent shown with an asterisk, it is preferably ortho or meta configuration, more preferably meta configuration.

While $R_{13}$ on the phenyl group may be in any configuration of ortho, meta and para relative to the substituent shown with an asterisk, it is preferably para or meta configuration, more preferably para configuration.

While the relationship between $R_{12}$ and $R_{13}$ on the phenyl group may be any of ortho, meta and para configurations, it is preferably ortho or meta configuration, more preferably ortho configuration.

As the "5- to 7-membered cyclic amino group" of the "optionally substituted 5- to 7-membered cyclic amino group" formed by $R_{10}$ and $R_{11}$ together with the nitrogen atom bonded thereto, those exemplified as the "optionally substituted 5- to 7-membered cyclic amino group", which is one embodiment of the "optionally substituted amino", which is the substituent that phenyl for $R_{11}$ optionally has, can be mentioned. The "5- to 7-membered cyclic amino group" is preferably 1-piperidinyl, morpholino and the like.

The "5- to 7-membered cyclic amino group" optionally has 1 to 3 (preferably 1 or 2) substituent(s) at substitutable position(s). As the substituent, those exemplified as the substituents for the aforementioned "substituted $C_{1-6}$ alkyl" for $R_1$ can be mentioned.

Examples of the physiologically acceptable salt of a compound represented by the formula (I) include salts with inorganic bases, salts with organic bases, salts with inorganic acids, salts with organic acids, salts with basic or acidic amino acids and the like. Preferable examples of the salts with inorganic bases include alkali metal salts such as sodium salt, potassium salt and the like; alkaline earth metal salts such as calcium salt, magnesium salt and the like; and aluminum salt, ammonium salt and the like. Preferable examples of the salts with organic bases include salts with trimethylamine, triethylamine, pyridine, picoline, ethanolamine, diethanolamine, triethanolamine, dicyclohexylamine, N,N'-dibenzylethylenediamine and the like. Preferable examples of the salts with inorganic acids include salts with hydrochloric acid, hydrobromic acid, nitric acid, sulfuric acid, phosphoric acid and the like. Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acids include salts with arginine, lysine, ornithine and the like, and preferable examples of the salts with acidic amino acid include salts with aspartic acid, glutamic acid and the like.

The compound represented by the formula (I) or a physiologically acceptable salt thereof may be a crystal or noncrystal and may be present in the form of hydrate and/or solvate. Such hydrate and/or solvate are also encompassed in the compound represented by the formula (I) or a physiologically acceptable salt thereof. A stoichiometric hydrate and a compound containing various amounts of water, which is obtained by a method such as freeze-drying, is also within the range of the compound represented by the formula (I) or physiologically acceptable salt thereof.

Some of the compounds represented by the formula (I) have an asymmetric carbon atom or geometric isomerism. Such stereoisomer, a mixture thereof and a racemate thereof are also encompassed in the present invention. A compound of the formula (I), which is substituted by an isotope, is also encompassed in the present invention.

In one embodiment, a preferable example of the compound represented by the formula (I) is a compound of the formula (I) specified by the following:

Y is a hydrogen atom or

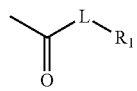

(wherein L is an oxygen atom or a bond, and $R_1$ is $C_{1-6}$ alkyl optionally substituted by $C_{6-14}$ aryl (preferably, phenyl));

$R_2$ is

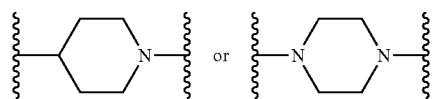

$R_3$ is —$NR_8$—$R_9$— or a bond (wherein $R_8$ is a hydrogen atom or $C_{1-6}$ alkyl, and $R_9$ is $C_{1-6}$ alkylene);

$R_4$, $R_5$, $R_6$ and $R_7$ are the same or different and each is a hydrogen atom or $C_{1-6}$ alkyl; and X is

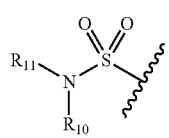

or a hydrogen atom (wherein $R_{10}$ is a hydrogen atom or $C_{1-6}$ alkyl;

$R_{11}$ is

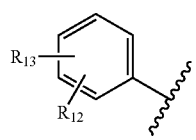

$C_{1-6}$ alkyl optionally substituted by $C_{3-8}$ cycloalkyl or a hydrogen atom, or $R_{10}$ and $R_{11}$ form, together with the nitrogen atom bonded thereto, an optionally substituted 5- to 7-membered cyclic amino group (preferably, 1-piperidinyl, morpholino etc.) (wherein $R_{12}$ is a hydrogen atom, furyl or thienyl;

$R_{13}$ is amino optionally mono- or di-substituted by $C_{1-6}$ alkyl or $C_{1-6}$ alkanoyl, 5 to 7-membered cyclic amino (preferably, 1-piperidinyl, 1-piperazinyl, morpholino etc.) optionally substituted by optionally esterified carboxy, $C_{1-6}$ alkyl optionally substituted by a halogen atom (e.g., fluorine atom, chlorine atom) or hydroxy, hydroxy, $C_{1-6}$ alkoxy optionally substituted by $C_{2-7}$ oxacycloalkyl, $C_{1-6}$ alkanoyl, $C_{6-10}$ aroyl or $N_3$)).

In another embodiment, preferable examples of a compound represented by the formula (I) is a compound of the following formula (IA):

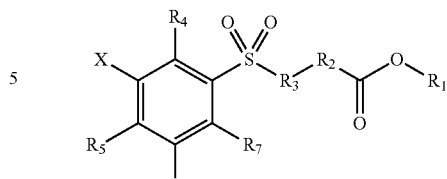

(IA)

(wherein $R_1$, $R_2$, $R_3$, $R_4$, $R_5$, $R_6$, $R_7$ and X mean the same as in the above-mentioned formula (I))

Preferable examples of the compound represented by the formula (IA) include a compound of the formula (IA) specified by the following:

$R_1$ is $C_{1-6}$ alkyl optionally substituted by $C_{6-14}$ aryl (preferably, phenyl);

$R_2$ is

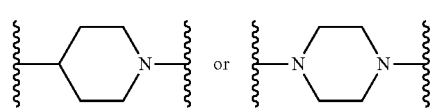

$R_3$ is —$NR_8$—$R_9$— or a bond (wherein $R_8$ is a hydrogen atom or $C_{1-6}$ alkyl, and $R_9$ is $C_{1-6}$ alkylene);

$R_4$, $R_5$, $R_6$ and $R_7$ are the same or different and each is a hydrogen atom or $C_{1-6}$ alkyl; and X is

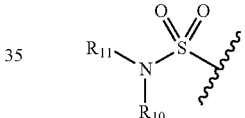

or a hydrogen atom (wherein $R_{10}$ is a hydrogen atom or $C_{1-6}$ alkyl;

$R_{11}$ is

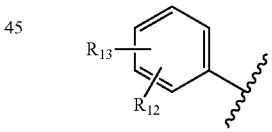

$C_{1-6}$ alkyl optionally substituted by $C_{3-8}$ cycloalkyl or a hydrogen atom, or $R_{10}$ and $R_{11}$ form, together with the nitrogen atom bonded thereto, an optionally substituted 5- to 7-membered cyclic amino group (preferably, 1-piperidinyl, morpholino etc.) (wherein $R_{12}$ is a hydrogen atom, furyl or thienyl;

$R_{13}$ is amino optionally mono- or di-substituted by $C_{1-6}$ alkyl or $C_{1-6}$ alkanoyl, 5- to 7-membered cyclic amino (preferably, 1-piperidinyl, 1-piperazinyl, morpholino etc.) optionally substituted by optionally esterified carboxy, $C_{1-6}$ alkyl optionally substituted by a halogen atom (e.g., fluorine atom, chlorine atom) or hydroxy, hydroxy, $C_{1-6}$ alkoxy optionally substituted by $C_{2-7}$ oxacycloalkyl, $C_{1-6}$ alkanoyl, $C_{6-10}$ aroyl or $N_3$)).

More preferable examples of the compound represented by the formula (IA) is a compound of the formula (IA), which is specified by the following:

R₁ is C₁₋₆ alkyl optionally substituted by C₆₋₁₄ aryl (preferably, phenyl);
R₂ is

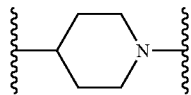

R₃ is —NR₈—R₉— (wherein R₈ is a hydrogen atom or C₁₋₆ alkyl, and R₉ is C₁₋₆ alkylene);
R₄, R₅, R₆ and R₇ are the same or different and each is a hydrogen atom or C₁₋₆ alkyl; and
X is,

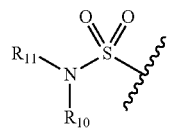

(wherein
R₁₀ is a hydrogen atom or C₁₋₆ alkyl;
R₁₁ is

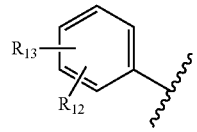

or C₁₋₆ alkyl optionally substituted by C₃₋₈ cycloalkyl
(wherein
R₁₂ is a hydrogen atom, furyl or thienyl; and
R₁₃ is amino optionally mono- or di-substituted by C₁₋₆ alkyl or C₁₋₆ alkanoyl, 5- to 7-membered cyclic amino (preferably, 1-piperidinyl, 1-piperazinyl, morpholino etc.) optionally substituted by optionally esterified carboxy, C₁₋₆ alkyl optionally substituted by a halogen atom (e.g., fluorine atom, chlorine atom) or hydroxy, hydroxy, C₁₋₆ alkoxy optionally substituted by C₂₋₇ oxacycloalkyl, C₁₋₆ alkanoyl, C₆₋₁₀ aroyl or N₃)).

As the compound represented by the formula (I) and a physiologically acceptable salt thereof, the following compounds and physiologically acceptable salts thereof can be specifically mentioned:

4-[3-(piperidine-1-sulfonyl)benzenesulfonyl]piperazine-1-carboxylic acid tert-butyl ester (Y043),
4-{[3-(piperidine-1-sulfonyl)benzenesulfonylamino]-methyl}-piperidine-1-carboxylic acid benzyl ester (Y053),
4-({methyl-[3-(methyl-p-tolylsulfamoyl)benzenesulfonyl]amino}methyl)piperidine-1-carboxylic acid tert-butyl ester (Y191),
4-[({3-[(4-tert-butylphenyl)methylsulfamoyl]benzenesulfonyl}methylamino)-methyl]piperidine-1-carboxylic acid tert-butyl ester (Y205),
4-{[3-(4-tert-butylphenylsulfamoyl)-2,4,5,6-tetramethylbenzenesulfonylamino]methyl}piperidine-1-carboxylic acid tert-butyl ester (Y335),
4-{[3-(piperidine-1-sulfonyl)benzenesulfonylamino]methyl}piperidine-1-carboxylic acid tert-butyl ester (Y029),
4-[(3-diethylsulfamoylbenzenesulfonylamino)methyl]piperidine-1-carboxylic acid tert-butyl ester (Y080),
4-{[3-(morpholine-4-sulfonyl)benzenesulfonylamino]methyl}piperidine-1-carboxylic acid tert-butyl ester (Y081),
4-[(3-sulfamoylbenzenesulfonylamino)methyl]piperidine-1-carboxylic acid tert-butyl ester (Y082),
4-(benzenesulfonylaminomethyl)piperidine-1-carboxylic acid tert-butyl ester (Y083),
4-{[3-(cyclohexylmethylsulfamoyl)benzenesulfonylamino]methyl}-piperidine-1-carboxylic acid tert-butyl ester (Y101),
4-[(3-phenylsulfamoylbenzenesulfonylamino)methyl]piperidine-1-carboxylic acid tert-butyl ester (Y098),
4-{[3-(4-methoxyphenylsulfamoyl)benzenesulfonylamino]methyl}piperidine-1-carboxylic acid tert-butyl ester (Y141),
4-{[3-(3-methoxyphenylsulfamoyl)benzenesulfonylamino]methyl}piperidine-1-carboxylic acid tert-butyl ester (Y142),
4-{[3-(2-methoxyphenylsulfamoyl)benzenesulfonylamino]methyl}piperidine-1-carboxylic acid tert-butyl ester (Y140),
4-{[3-(4-trifluoromethylphenylsulfamoyl)benzenesulfonylamino]methyl}-piperidine-1-carboxylic acid tert-butyl ester (Y145),
4-{[3-(2-acetylaminophenylsulfamoyl)benzenesulfonylamino]methyl}-piperidine-1-carboxylic acid tert-butyl ester (Y147),
4-[(3-p-tolylsulfamoylbenzenesulfonylamino)methyl]piperidine-1-carboxylic acid tert-butyl ester (Y155),
4-{[3-(4-tert-butylphenylsulfamoyl)benzenesulfonylamino]methyl}piperidine-1-carboxylic acid tert-butyl ester (Y177),
4-{[3-(4-piperidin-1-yl-phenylsulfamoyl)benzenesulfonylamino]methyl}piperidine-1-carboxylic acid tert-butyl ester (Y224),
4-{[3-(4-diethylaminophenylsulfamoyl)benzenesulfonylamino]methyl}-piperidine-1-carboxylic acid tert-butyl ester (Y186),
4-{[3-(4-dimethylaminophenylsulfamoyl)benzenesulfonylamino]methyl}-piperidine-1-carboxylic acid tert-butyl ester (Y178),
4-{[3-(4-morpholin-4-yl-phenylsulfamoyl)benzenesulfonylamino]methyl}-piperidine-1-carboxylic acid tert-butyl ester (Y185),
4-{[3-(4-acetylphenylsulfamoyl)benzenesulfonylamino]methyl}piperidine-1-carboxylic acid tert-butyl ester (Y192),
4-({3-[4-(1-hydroxyethyl)phenylsulfamoyl]benzenesulfonylamino}methyl)-piperidine-1-carboxylic acid tert-butyl ester (Y195),
4-{[3-(4-hydroxyphenylsulfamoyl)benzenesulfonylamino]methyl}piperidine-1-carboxylic acid tert-butyl ester (Y196),
4-{[3-(4-oxanylmethoxyphenylsulfamoyl)benzenesulfonylamino]methyl}-piperidine-1-carboxylic acid tert-butyl ester (Y198),
4-{[3-(4-azidophenylsulfamoyl)benzenesulfonylamino]methyl}piperidine-1-carboxylic acid tert-butyl ester (Y241),
4-(4-{3-[(1-tert-butoxycarbonylpiperidin-4-ylmethyl)sulfamoyl]benzenesulfonylamino}phenyl)piperazine-1-carboxylic acid tert-butyl ester (Y260),
4-({3-[4-(4-benzoylpiperazin-1-yl)phenylsulfamoyl]benzenesulfonylamino}methyl)piperidine-1-carboxylic acid tert-butyl ester (Y366),
4-{[3-(4-dimethylamino-3-furan-2-yl-phenylsulfamoyl)benzenesulfonylamino]methyl}piperidine-1-carboxylic acid tert-butyl ester (Y244),
4-{[3-(3-furan-2-yl-4-piperidin-1-yl-phenylsulfamoyl)benzenesulfonylamino]methyl}piperidine-1-carboxylic acid tert-butyl ester (Y250),
4-{[3-(3-furan-2-yl-phenylsulfamoyl)benzenesulfonylamino]methyl}piperidine-1-carboxylic acid tert-butyl ester (Y284), and
4-{[3-(3-thiophen-2-yl-phenylsulfamoyl)benzenesulfonylamino]methyl}piperidine-1-carboxylic acid tert-butyl ester (Y296).

In a further aspect, as the compound represented by the formula (I) and a physiologically acceptable salt thereof, the following compounds and physiologically acceptable salts thereof can be mentioned:

4-{[3-(4-dimethylamino-3-furan-2-yl-phenylsulfamoyl)benzenesulfonylamino]methyl}piperidine (Y516), and 4-{[3-(4-dimethylamino-3-furan-2-yl-phenylsulfamoyl)benzenesulfonylamino]methyl}-1-butyryl-piperidine (Y639).

Now the production methods of the compounds of the present invention are explained below.

Of the compounds of the present invention, a compound represented by the formula (IA) can be produced, for example, by production method A shown below.

[Production method A]: A method of producing a compound represented by the aforementioned formula (IA), comprising reacting a compound represented by the following formula (II)

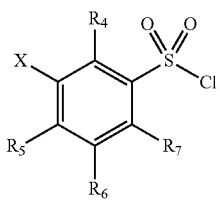

(wherein $R_4$, $R_5$, $R_6$, $R_7$ and X mean the same as in the above-mentioned formula (I)) with a compound represented by the following formula (III)

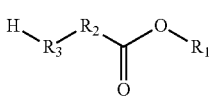

(wherein $R_1$, $R_2$ and $R_3$ mean the same as in the above-mentioned formula (I)).

The reaction of a compound of the formula (II) with a compound of the formula (III) is performed without solvent or in a suitable solvent. The solvent to be used is, for example, toluene, xylene, diethyl ether, tetrahydrofuran, dioxane, dichloromethane, chloroform and the like. These solvents are used alone, or in a mixture of two or more kinds thereof. The reaction temperature is generally −40° C.-200° C., preferably −20° C.-70° C., more preferably 1° C.-30° C.

A compound of the formula (IA) wherein $R_3$ is —$NR_8$—$R_9$— and $R_8$ is $C_{1-6}$ alkyl (i.e., a compound represented by the following formula (I-a)

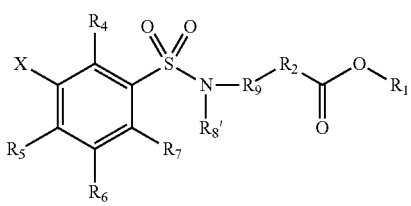

(wherein $R_1$, $R_2$, $R_3$, $R_4$, $R_5$, $R_6$, $R_7$ and $R_9$ mean the same as in the above-mentioned formula (I), and $R_{8'}$ is $C_{1-6}$ alkyl) can also be produced by, for example, the following production method B.

[Production method B]: A method of producing a compound represented by the aforementioned formula (I-a), comprising reacting a compound represented by the following formula (I-b)

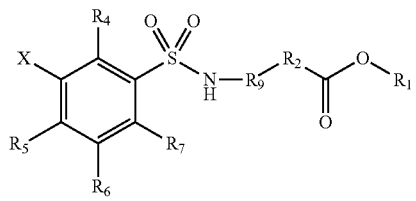

(wherein $R_1$, $R_2$, $R_4$, $R_5$, $R_6$, $R_7$ and $R_9$ mean the same as in the above-mentioned formula (I))
with a compound represented by $R_{8'}$—I (wherein $R_{8'}$ is $C_{1-6}$ alkyl)
to introduce an alkyl group into an amino group.

The compound represented by the formula I-b is a compound the formula (IA) wherein $R_8$ is a hydrogen atom, which can be produced by the above-mentioned production method A.

The reaction of a compound of the formula (I-b) with $R_{8'}$—I is performed without solvent or in a suitable solvent. The solvent to be used is, for example, toluene, xylene, diethyl ether, tetrahydrofuran, dioxane, dichloromethane, chloroform and the like. These solvents are used alone, or in a mixture of two or more kinds thereof. This reaction is performed in the presence of a base where necessary. Specific examples of the base include sodium hydride, calcium hydride, potassium t-butoxide, sodium ethoxide, sodium methoxide, butyllithium, phenyllithium, lithiumdiisopropylamide, lithium hydroxide, potassium hydroxide, sodium hydroxide, lithium hydride and the like. The reaction temperature is generally −40° C.-200° C., preferably −20° C.-70° C., more preferably 1° C.-30° C.

In addition, a compound represented by the formula (IA) wherein X is

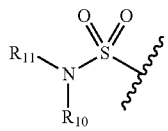

(wherein $R_{10}$ and $R_{11}$ mean the same as in the above-mentioned formula (I))
(i.e., a compound of the following formula (I-c)

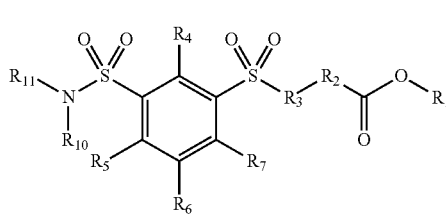

(wherein $R_1$, $R_2$, $R_3$, $R_4$, $R_5$, $R_6$, $R_7$, $R_{10}$ and $R_{11}$ mean the same as in the above-mentioned formula (I))
may be produced, for example, by the following production method C.

[Production method C]: A method of producing a compound represented by the aforementioned formula (I-c), comprising reacting a compound represented by the following formula (I-d)

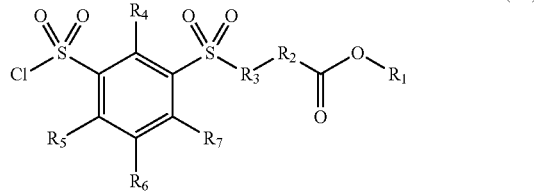

(I-d)

(wherein $R_1$, $R_2$, $R_3$, $R_4$, $R_5$, $R_6$ and $R_7$ mean the same as in the above-mentioned formula (I))
with a compound represented by the formula (IV)

(IV)

(wherein $R_{10}$ and $R_{11}$ mean the same as in the above-mentioned formula (I)).

The compound represented by the formula I-d is a compound of the formula (IA) wherein X is Cl—$SO_2$—, which can be produced according to the above-mentioned production method A or B.

The reaction of a compound of the formula I-d with a compound represented by the formula IV is performed without solvent or in a suitable solvent. The solvent to be used is, for example, toluene, xylene, diethyl ether, tetrahydrofuran, dioxane, dichloromethane, chloroform and the like. These solvents are used alone, or in a mixture of two or more kinds thereof. This reaction is performed in the presence of a base where necessary. Specific examples of the base include organic bases such as triethylamine, imidazole, N-methylimidazole, p-dimethylaminopyridine, N-methylmorpholine and the like, inorganic bases such as sodium hydrogen carbonate, potassium hydrogen carbonate, sodium bicarbonate, potassium bicarbonate and sodium hydroxide, and the like. The reaction temperature is generally −40° C.-200° C., preferably −20° C.-70° C., more preferably 1° C.-30° C.

A compound of the formula (IV) wherein $R_{10}$ is a hydrogen atom (i.e., $R_{11}$—$NH_2$) can be obtained by a catalytic reduction of $R_{11}$—$NO_2$ in an appropriate solvent under a hydrogen atmosphere, using a metal catalyst such as palladium and the like. The solvent to be used is, for example, toluene, xylene, tetrahydrofuran, dioxane, methylene chloride, chloroform, acetonitrile, methanol, ethanol, ethyl acetate and the like. These solvents are used alone, or in a mixture of two or more kinds thereof. The reaction temperature is generally −40° C.-200° C., preferably −20° C.-70° C., more preferably 1° C.-30° C.

A compound the formula (I-c) wherein $R_{10}$ is $C_{1-6}$ alkyl (i.e., a compound represented by the following formula (I-e)

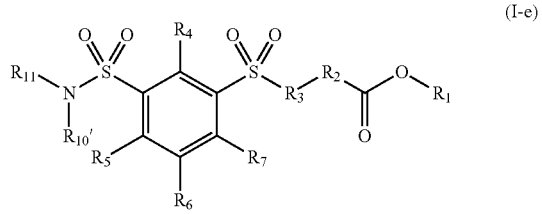

(I-e)

(wherein $R_1$, $R_2$, $R_3$, $R_4$, $R_5$, $R_6$, $R_7$ and $R_{11}$ mean the same as in the above-mentioned formula (I) and $R_{10'}$ is $C_{1-6}$ alkyl))

can also be produced by, for example, the following production method D.

[Production method D]: A method of producing a compound represented by the aforementioned formula (I-e), comprising reacting a compound represented by the following formula (I-f)

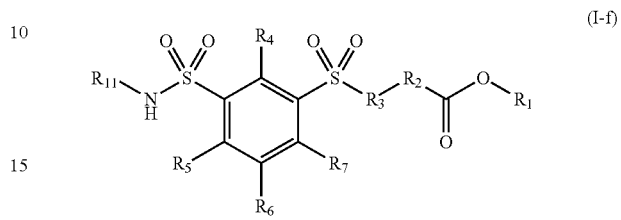

(I-f)

(wherein $R_1$, $R_2$, $R_3$, $R_4$, $R_5$, $R_6$, $R_7$ and $R_{11}$ mean the same as in the above-mentioned formula (I))
with $R_{10'}$—I (wherein $R_{10'}$ is $C_{1-6}$ alkyl)
to introduce an alkyl group into an amino group.

The compound represented by the formula I-f is a compound of the formula (I-c) wherein $R_{10}$ is a hydrogen atom, which can be produced by the above-mentioned production method A, B or C.

The reaction of a compound of the formula (I-f) with $R_{10'}$—I is performed without solvent or in a suitable solvent. The solvent to be used is, for example, toluene, xylene, diethyl ether, tetrahydrofuran, dioxane, dichloromethane, chloroform and the like. These solvents are used alone, or in a mixture of two or more kinds thereof. This reaction is performed in the presence of a base where necessary. Specific examples of the base include sodium hydride, calcium hydride, potassium t-butoxide, sodium ethoxide, sodium methoxide, butyllithium, phenyllithium, lithiumdiisopropylamide, lithium hydroxide, potassium hydroxide, sodium hydroxide, lithium hydride and the like. The reaction temperature is generally −40° C.-200° C., preferably −20° C.-70° C., more preferably 1° C.-30° C.

Of the compounds represented by the formula (I), a compound wherein Y is a hydrogen atom can be synthesized by reacting a compound of the formula (IA) with an acid in a solvent or without solvent to eliminate a group represented by the following formula

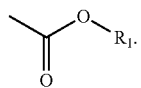

As the acid, trifluoroacetic acid, hydrochloric acid, formic acid, methanesulfonic acid, tosylic acid and the like can be mentioned, with preference given to trifluoroacetic acid, formic acid and hydrochloric acid. The solvent to be used is, for example, toluene, xylene, diethyl ether, tetrahydrofuran, dioxane, dichloromethane, chloroform and the like. These solvents are used alone, or in a mixture of two or more kinds thereof. The reaction temperature is generally −40° C.-200° C., preferably −20° C.-70° C., more preferably 1° C.-30° C.

Of the compounds represented by the formula (I), a compound wherein Y is

can be produced by condensing a compound represented by the formula (I) wherein Y is a hydrogen atom, which can be produced by the above-mentioned method etc., with carboxylic acid represented by the following formula

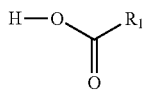

in a solvent or without solvent. The amount of the carboxylic acid to be used is about 1-5 mol per 1 mol of the compound represented by the formula (I) wherein Y is a hydrogen atom. The solvent to be used is, for example, toluene, xylene, diethyl ether, tetrahydrofuran, dioxane, dichloromethane, chloroform and the like. These solvents are used alone, or in a mixture of two or more kinds thereof. The reaction temperature is generally −40° C.-200° C., preferably −20° C.-70° C., more preferably 1° C.-30° C.

In the condensation reaction, it is preferable to use an appropriate dehydrating condensing agent. Examples of the dehydrating condensing agent include N,N'-dicyclohexylcarbodiimide (DCC), N,N'-diisopropylcarbodiimide (DIC), 1-ethyl-3-(3-dimethylaminopropyl)carbodiimide (EDC), 1-ethyl-3-(3-dimethylaminopropyl)carbodiimide hydrochloride (EDC-HCl), 1H-benzotriazol-1-yloxytris(dimethylamino)phosphonium hexafluorophosphate (BOP), 1H-benzotriazol-1-yl-oxytripyrrolidinophosphonium hexafluorophosphate (PyBOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU), O-(7-azabenzotriazol-1-yl)-N,N,N',N'-tetramethyluronium tetrafluoroborate (TATU), 1,1'-carbonylbis-1H-imidazole (CDI) and the like.

The condensation reaction is preferably performed in the presence of an appropriate base. Examples of the base include tertiary amines, for example, trialkylamines such as trimethylamine, triethylamine, N,N-diisopropylethylamine (DIEA) and the like, heterocyclic tertiary amines such as N-methylmorpholine, pyridine and the like, and the like. The amount of the base to be used is about 1-5 mol per 1 mol of the compound represented by the formula (I) wherein Y is a hydrogen atom.

Of the compounds represented by the formula (I), a compound wherein Y is a carboxyl group can be obtained by using a compound wherein R₁ is a hydrogen atom as each starting material in the production methods A-D, or hydrolyzing a compound of the formula (IA).

Each compound obtained by the above-mentioned production method is isolated and purified according to a conventional method such as extraction, silica gel column chromatography, recrystallization and reprecipitation. As an extraction solvent, diethyl ether, ethyl acetate, chloroform, dichloromethane, toluene and the like are used. For purification by silica gel column chromatography, silica gel, alumina and the like, which are acidic, basic or after various chemical treatments, are used and, for example, hexane/ethyl acetate, hexane/chloroform, ethyl acetate/methanol, chloroform/methanol, acetonitrile/water, methanol/water and the like can be used as an eluent.

When the compound of the formula (I) is a racemate, it can be separated and purified into each enantiomer according to a conventional method such as chromatography using an optically active column, optical resolution method by optically active acid, synthetic chiral resolution reagent and the like, preferential crystallization method, diastereomer method and the like. For example, separation into an enantiomer using an optically active acid is performed by forming a diastereomer salt according to a conventional method, separating into two kinds of diastereomer salts, and converting them to free bases. Examples of the optically active acid to be used as an optical resolution reagent include (+)- or (−)-camphoric acid, (1S)-(+)- or (1R)-(−)-camphor-10-sulfonic acid, L-(+)- or D-(−)-tartaric acid, (+)- or (−)-mandelic acid, (S)-(−)- or (R)-(+)-malic acid, L-pyroglutamic acid, (S)-(+)- or (R)-(−)-1,1'-binaphthyl-2,2'-diyl, (+)-dibenzoyl-D-tartaric acid or (−)-dibenzoyl-L-tartaric acid and the like.

In the above-mentioned production method, where necessary, each reaction can also be performed after introduction of a protecting group into a functional group (hydroxy group, carboxyl group, amino group etc.) contained in the starting compound. By subjecting the obtained reaction product to a deprotection treatment, the object compound can be obtained. The protection and deprotection of the functional group can be performed easily by those of ordinary skill in the art according to a conventional method.

While the compound of the formula (I) is obtained in the form of a free base or an acid addition salt depending on the kind of the functional group present in the structural formula, selection of the starting compound, and reaction treatment conditions, it can be converted to the compound of the formula (I) according to a conventional method. In addition, the compound of the formula (I) can be led to an acid addition salt by treating with an appropriate acid according to a conventional method depending on the kind of the functional group present in the structural formula.

A pharmaceutical composition containing the compound of the present invention is explained below.

The present invention also provides a pharmaceutical composition containing a compound represented by the formula (I) or a physiologically acceptable salt thereof as an active ingredient, and a pharmaceutically acceptable excipient, diluent or carrier. A compound represented by the formula (I) or physiologically acceptable salt thereof can be prepared into a pharmaceutical composition together with a pharmaceutically acceptable, conventionally known excipient, diluent, carrier and the like.

As the excipient, for example, starch, lactose, sucrose, mannit, carboxymethylcellulose, cornstarch, inorganic salts and the like can be mentioned, and one kind alone or two or more kinds thereof are used in combination.

Examples of the diluent include distilled water for injection, saline, aqueous glucose solution, vegetable oil for injection, propylene glycol, polyethylene glycol and the like, and one kind alone or two or more kinds thereof are used in combination.

As the carrier, for example, magnesium carbonate, magnesium stearate, talc, sucrose, lactose, pectin, dextrin, starch, gelatin, tragacanth, methylcellulose, carboxymethylcellulosesodium and the like can be mentioned, and one kind alone or two or more kinds thereof are used in combination.

Besides the above-mentioned, additives such as binder, disintegrant, surfactant, absorption promoter, moisturizer, adsorbent, lubricant, filler, expander, misturizer, antiseptic, stabilizer, emulsifier, solubilizer, salt for adjusting osmotic pressure and the like can be appropriately selected and used according to the unit dosage of the obtained preparation. Furthermore, the pharmaceutical composition of the present invention may be blended, where necessary, with colorant, preservative, flavor, flavoring agent, sweetening agent and the like to give a preparation.

Examples of the dosage form of the pharmaceutical composition of the present invention include, regardless of whether it is for oral or parenteral (e.g., topical, rectal, intravenous administration etc.) administration, tablet (including sugar-coated tablet, film-coated tablet), powder, granule, capsule (including soft capsule), liquid, injection, suppository, sustained-release preparation and the like. When it is prepared as an injection form, it can be administered by intravenous, intramuscular, subcutaneous, intraorgan, intranasal, intradermal, instillation, intracerebral, intrarectal, intravaginal, intraperitoneal, intratumor, tumor proximal administration and the like, or it can be administered directly to the lesion.

When the pharmaceutical composition of the present invention is a liquid, it may be preserved by cryopreservation or after removing water by freeze-drying and the like. A freeze-dry preparation is used upon redissolution by adding, when in use, distilled water for injection and the like.

While the dose of the above-mentioned pharmaceutical composition can be appropriately determined according to a desired treatment effect, administration method, treatment period, age, sex and other conditions of patients, and the like, it is generally about 1 pg-1 g, preferably about 1 pg-10 mg, more preferably 1 pg-1 μg, more preferably about 1 pg-500 ng, about 1 pg-50 ng, about 1 pg-1 ng, of the compound of the present invention as an active ingredient, per 1 kg body weight per day for an adult human. The pharmaceutical composition of the present invention can be administered once or in several portions per day.

While the content of a compound represented by the formula (I) or a salt thereof in the pharmaceutical composition of the present invention varies depending on the preparation form and can be appropriately determined based on the dose generally employed, it is, for example, 0.0001-99.9999 wt % and the like.

Since a compound represented by the formula (I) or a physiologically acceptable salt thereof has a TGF-β signal transduction inhibitory activity, it can be used as a TGF-β signal transduction inhibitor, and as an agent for the treatment and/or prophylaxis of TGF-β-related diseases in mammals. The "signal transduction" is a process in which binding of a ligand to a receptor is translated into a physiological change. To be specific, it means a process in which binding of TGF-β to a receptor activates Smad3/Smad4 complex, the complex binds to a target sequence (CAGA sequence), and transcription of the gene at the downstream thereof is regulated (up-regulated or down-regulated). TGF-β-related disease means a disease wherein the pathology formation factor includes excessive TGF-β or TGF-β signal. TGF-β forms pathology of sclerotic diseases accompanied by fibrillization of tissue such as liver fibrillization/cirrhosis, arteriosclerosis, lung fibrosis (idiopathic pulmonary fibrosis etc.), skin fibrosis, scleroderma, renal failure (glomerulonephritis), rheumatoid arthritis, diabetic nephropathy, metabolic diseases (hemochromatosis, Wilson's disease etc.), cancer (hysteromyoma etc.) and the like, by potently promoting collagen production in mesenchymal cells. Thus, specific examples of the TGF-β-related disease include sclerotic diseases accompanied by fibrillization of tissue such as liver fibrillization/cirrhosis, arteriosclerosis, pulmonary fibrosis (idiopathic pulmonary fibrosis etc.), skin fibrosis, scleroderma, renal failure (glomerulonephritis), rheumatoid arthritis, diabetic nephropathy, metabolic diseases (hemochromatosis, Wilson's disease etc.), cancer (hysteromyoma etc.) and the like.

Since the compound represented by the formula (I) or a physiologically acceptable salt thereof is low toxic and safe, it can be administered as it is as a medicament, or after mixing with a pharmaceutically acceptable carrier known per se and the like to mammals including human (e.g., horse, bovine, dog, cat, rat, mouse, rabbit, swine, monkey, human etc.) to prevent or treat TGF-β-related diseases in the mammals.

The present invention is explained in more detail in the following by referring to Reference Examples, Examples and Experimental Examples, which are not to be construed as limitative.

EXAMPLES

Example 1

4-{[3-(4-tert-butylphenylsulfamoyl)-2,4,5,6-tetramethylbenzenesulfonylamino]methyl}piperidine-1-carboxylic acid tert-butyl ester (Y335)

2,4,5,6-tetramethylbenzenedisulfonyldichloride (1.2 g, 3.6 mmol) was dissolved in dichloromethane (18 ml), and the mixture was stirred under ice-cooling. Then, a solution (18 ml) of 1-Boc-4-(aminomethyl)piperidine (620 μl, 2.90 mmol) in dichloromethane was added, and the mixture was stirred under ice-cooling for 2 hr. Then, the solvent was concentrated under reduced pressure, and the obtained residue was purified by silica gel chromatography (eluent; hexane:ethyl acetate (2:1)) to give compound Y321 (yield; 533 mg, 29%). Compound Y321 (88 mg, 0.17 mmol) was dissolved in dichloromethane (3 ml), tert-butylaniline (40 μl, 0.26 mmol) and triethylamine (72 μl, 0.52 mmol) were added, and the mixture was stirred at room temperature for 4 hr. Then, the solvent was concentrated under reduced pressure and the obtained residue was purified by silica gel chromatography (eluent; chloroform:methanol (40:1)) to give the title compound (yield; 86 mg, 80%).

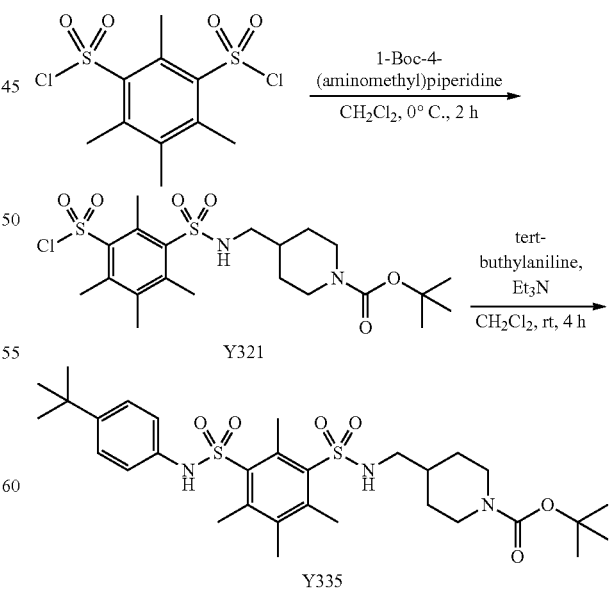

$^1$H NMR (500 MHz, CDCl$_3$) δ7.21 (dd, 2H, J=8.5, 3.0 Hz), 7.1 (bs, 1H), 6.85 (dd, 2H, J=8.5, 3.0 Hz), 4.70 (dd, 1H J=7.0, 6.0 Hz), 4.06 (bs, 2H), 2.86 (s, 3H), 2.64-2.60 (m, 9H), 2.25 (s, 3H), 1.60-1.50 (m, 3H), 1.43 (s, 9H), 1.23 (s, 9H), 1.04-0.96 (m, 2H)

$^{13}$C NMR (125 MHz, CDCl$_3$) δ154.9, 148.8, 141.9, 141.5, 139.6, 139.2, 138.3, 136.6, 133.4, 126.4, 121.6, 79.7, 77.5, 48.4, 36.7, 34.5, 31.4, 29.7, 28.6, 21.0, 20.4, 20.1, 17.4

HRMS (FAB-) m/z: [M-H]$^-$ calcd for C$_{31}$H$_{46}$N$_3$O$_6$S$_2$, 620.2828. found, 620.2977

Example 2

4-{[3-(4-piperidin-1-yl-phenylsulfamoyl)benzene-sulfonylamino]methyl}piperidine-1-carboxylic acid tert-butyl ester (Y224)

4-Fluoronitrobenzene (323 mg, 2.3 mmol) was dissolved in DMSO (5 ml), potassium carbonate (475 mg, 3.5 mmol) and piperidine (460 μl, 4.6 mmol) were added, and the mixture was stirred at 90° C. for 9 hr. Then, water was added to the reaction solution, and the mixture was extracted twice with ethyl acetate. The organic layer was washed twice with saturated aqueous NaCl. The organic layer was dried over Na$_2$CO$_3$, the solvent was evaporated to give compound Y197 (yield; 472 mg, 100%). Compound Y197 was dissolved in ethyl acetate (20 ml), Pd/C (186 mg) was added, and the mixture was stirred under a hydrogen atmosphere at room temperature for 3 hr. Then, the reaction solution was filtered through celite, the filtrate was concentrated under reduced pressure, and the obtained residue was purified by silica gel chromatography (eluent; chloroform:methanol (40:1)) to give compound Y222 (yield, quantitative, 394 mg). Compound Y491 (mentioned later) (80 mg, 0.18 mmol) was dissolved in dichloromethane (2 ml), compound Y222 (100 mg, 0.58 mmol) was added, and the mixture was stirred at room temperature for 5 hr. Then, the solvent was concentrated under reduced pressure, and the obtained residue was purified by silica gel chromatography (eluent; chloroform:methanol (35:1)) to give the title compound (yield; 68 mg, 64%).

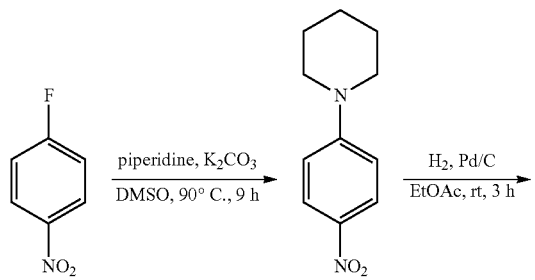

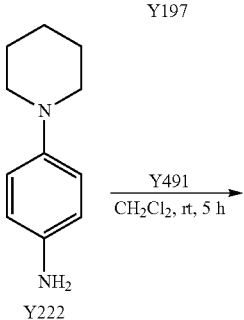

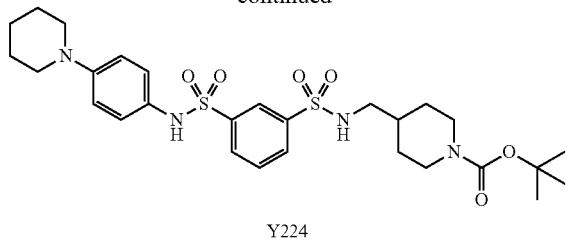

Y224

$^1$H NMR (500 MHz, CDCl$_3$) δ8.40 (s, 1H), 8.0 (d, 1H, J=8.0 Hz), 7.70 (d, 1H, J=8.5 Hz), 7.52 (dd, 1H, J=8.0, 7.5 Hz), 6.92 (dd, 2H, J=9.0, 3.5 Hz), 6.77 (dd, 2H, J=9.0, 6.5 Hz), 5.33 (t, 1H, J=6.0 Hz), 4.07 (bs, 2H), 3.11-3.09 (m, 4H), 2.79-2.64 (m, 4H), 1.69-1.53 (m, 10H), 1.43 (s, 9H), 1.09-1.01 (m, 2H)

$^{13}$C NMR (125 MHz, CDCl$_3$) δ154.9, 141.6, 140.8, 131.4, 130.9, 129.8, 125.8, 125.7, 79.7, 77.4, 48.7, 36.6, 29.6, 28.6, 25.7, 24.2

HRMS (FAB-) m/z: [M-H]$^-$ calcd for C$_{28}$H$_{39}$N$_4$O$_6$S$_2$, 591.2311. found, 591.2324

Example 3

4-{[3-(4-morpholin-4-yl-phenylsulfamoyl)benzene-sulfonylamino]methyl}piperidine-1-carboxylic acid tert-butyl ester (Y185)

4-Fluoronitrobenzene (382 mg, 2.7 mmol) was dissolved in DMSO (7 ml), potassium carbonate (561 mg, 4.0 mmol) and morpholine (472 mg, 5.4 mmol) were added, and the mixture was stirred at 90° C. overnight. Then, water was added to the reaction solution, and the mixture was extracted twice with ethyl acetate. The organic layer was washed twice with saturated aqueous NaCl. The organic layer was dried over Na$_2$CO$_3$, the solvent was evaporated, and the obtained residue was purified by silica gel chromatography (eluent; hexane:ethyl acetate (2:1)) to give compound Y180 (yield; 493 mg, 88%). Compound Y180 (483 mg, 2.3 mmol) was dissolved in methanol (25 ml), Pd/C (205 mg) was added, and the mixture was stirred under a hydrogen atmosphere at room temperature overnight. Then, the reaction solution was filtered through celite, the filtrate was concentrated under reduced pressure, and the obtained residue was purified by silica gel chromatography (eluent; hexane:ethyl acetate (1:2)) to give compound Y183 (yield; 358 mg, 87%). Compound Y491 (mentioned later) (134 mg, 0.3 mmol) was dissolved in dichloromethane (4 ml), compound Y183 (158 mg, 0.9 mmol) and triethylamine (123 μl, 0.9 mmol) were added, and the mixture was stirred at room temperature for 45 min. Then, the solvent was concentrated under reduced pressure, and the obtained residue was purified by silica gel chromatography (eluent; chloroform:methanol (22:1)) to give the title compound (yield; 120 mg, 69%).

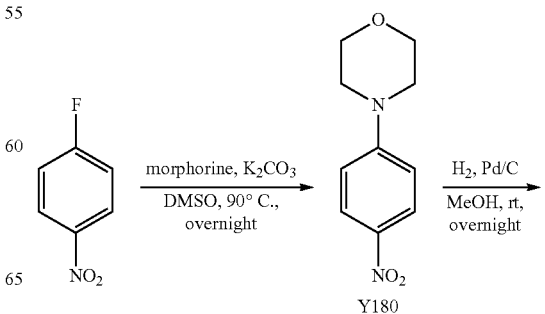

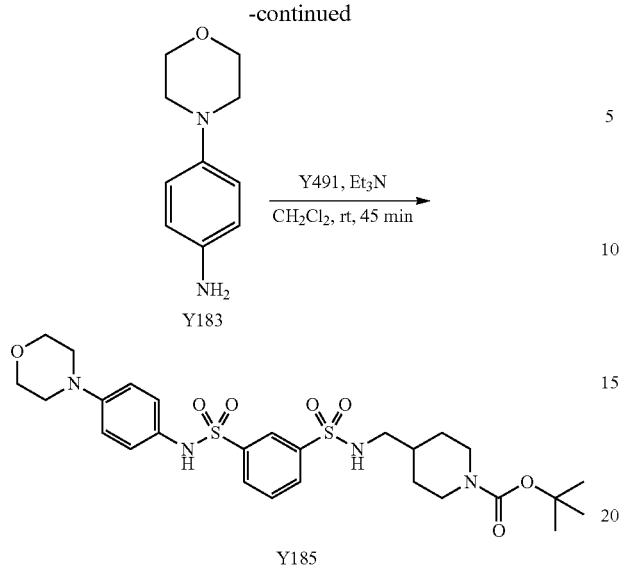

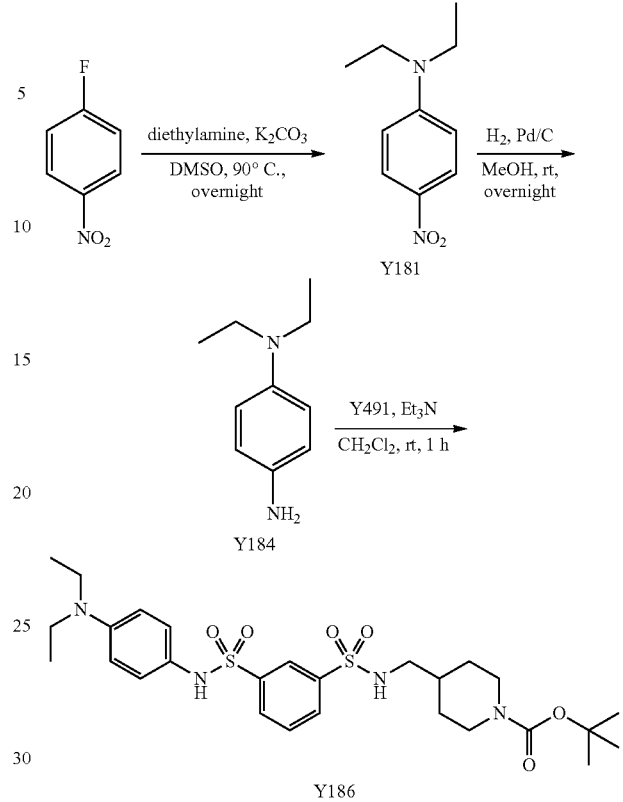

$^1$H NMR (500 MHz, CDCl$_3$) δ8.43 (s, 1H), 8.00 (d, 1H, J=8.0 Hz), 7.70 (d, 1H, J=8.0 Hz), 7.53 (t, 1H, J=8.0 Hz), 7.43 (bs, 1H), 6.98 (dd, 2H, J=9.0, 3.5 Hz), 6.76 (dd, 2H, J=9.0, 3.5 Hz), 5.55 (dd, 1H, J=6.5, 6.0 Hz), 4.05 (bs, 2H), 3.83-3.81 (m, 4H), 3.10-3.08 (m, 4H), 2.80-2.63 (m, 4H), 1.64-1.54 (m, 3H), 1.42 (s, 9H), 1.86-1.01 (m, 2H)

$^{13}$C NMR (125 MHz, CDCl$_3$) δ155.0, 150.1, 141.6, 140.8, 131.3, 131.0, 129.8, 127.4, 125.8, 125.6, 116.2, 79.7, 66.9, 58.6, 50.9, 49.2, 48.7, 36.5, 29.6, 28.6, 18.5

HRMS (FAB-) m/z: [M-H]$^-$ calcd for C$_{27}$H$_{37}$N$_4$O$_7$S$_2$, 593.2104. found, 593.2197

Example 4

4-{[3-(4-diethylaminophenylsulfamoyl)benzenesulfonylamino]methyl}-piperidine-1-carboxylic acid tert-butyl ester (Y186)

4-Fluoronitrobenzene (316 mg, 2.2 mmol) was dissolved in DMSO (5 ml), potassium carbonate (464 mg, 3.4 mmol) and diethylamine (327 mg, 4.4 mmol) were added, and the mixture was stirred at 90° C. overnight. Then, water was added to the reaction solution, and the mixture was extracted twice with ethyl acetate. The organic layer was washed twice with saturated aqueous NaCl. The organic layer was dried over Na$_2$CO$_3$, the solvent was evaporated, and the obtained residue was purified by silica gel chromatography (eluent; hexane:ethyl acetate (2:1)) to give compound Y181 (yield; 386 mg, 89%). Compound Y181 (369 mg, 1.9 mmol) was dissolved in methanol (20 ml), Pd/C (141 mg) was added, and the mixture was stirred under a hydrogen atmosphere at room temperature overnight. Then, the reaction solution was filtered through celite, the filtrate was concentrated under reduced pressure, and the obtained residue was purified by silica gel chromatography (eluent; hexane:ethyl acetate (1:1)) to give compound Y184 (yield; 280 mg, 90%). Compound Y491 (mentioned later) (158 mg, 0.35 mmol) was dissolved in dichloromethane (5 ml), compound Y184 (143 mg, 0.9 mmol) and triethylamine (145 μl, 1.0 mmol) were added, and the mixture was stirred at room temperature for 1 hr. Then, the solvent was concentrated under reduced pressure, and the obtained residue was purified by silica gel chromatography (eluent; chloroform:methanol (30:1)) to give the title compound (yield; 24 mg, 12%).

$^1$H NMR (500 MHz, CDCl$_3$) δ8.44 (s, 1H), 8.00 (d, 1H, J=8.0 Hz), 7.30 (d, 1H, J=8.0 Hz), 7.53 (t, 1H, J=8.0 Hz), 7.09 (bs, 1H), 6.87 (d, 2H, J=9.0 Hz), 6.49 (d, 2H, J=8.5 Hz), 5.45 (t, 1H, J=6.5 Hz), 4.06 (bs, 2H), 3.28 (dd, 4H, J=14.0, 7.0 Hz), 2.81-2.63 (m, 4H), 1.66-1.57 (m, 3H), 1.43 (s, 9H), 1.13 (t, 6H, J=7.0 Hz), 1.08-0.99 (m, 2H)

$^{13}$C NMR (125 MHz, CDCl$_3$) δ154.9, 147.1, 141.5, 141.1, 131.9, 131.0, 129.7, 126.9, 125.8, 122.8, 112.1, 79.6, 79.5, 77.4, 48.7, 44.5, 36.6, 29.6, 28.6, 12.6

HRMS (FAB-) m/z: [M-H]$^-$ calcd for C$_{27}$H$_{40}$N$_4$O$_6$S$_2$, 579.2311. found, 579.2360

Example 5

4-{[3-(4-dimethylamino-3-furan-2-yl-phenylsulfamoyl)benzenesulfonylamino]methyl}piperidine-1-carboxylic acid tert-butyl ester (Y244)

To a solution (200 ml) of N-methyl-4-nitroaniline (5.61 g, 37 mmol) in acetonitrile was added a solution (100 ml) of N-bromosuccinimide (6.9 g, 38 mmol) in acetonitrile under ice-cooling and the mixture was stirred for 30 min. Then, the solvent was concentrated under reduced pressure, water was added to the obtained residue, and the mixture was extracted twice with ethyl acetate. The organic layer was washed twice with saturated brine, and the organic layer was dried over Na$_2$CO$_3$. The solvent was evaporated, and the residue was recrystallized from ethyl acetate/hexane solvent to give compound Y495 (yield; quantitative, 10.6 g). Compound Y495 (1.0 g, 4.3 mmol) was dissolved in DMF (40 ml). Then, 2-furylboronic acid (500 mg, 4.3 mmol), Pd(PPh$_3$)$_4$ (500 mg, 10 mol %) and 2M K$_2$CO$_3$ (5 ml) were added under a nitrogen stream, and the mixture was stirred under a nitrogen stream at 80° C. for 23 hr.

Then, water was added to the reaction solution, and the mixture was extracted twice with ethyl acetate. The organic layer was washed twice with saturated aqueous NaCl. The organic layer was dried over Na₂CO₃, the solvent was evaporated, and the obtained residue was purified by silica gel chromatography (eluent; hexane:ethyl acetate (5:1) to give compound Y496 (yield; 785 mg, 83%).

Compound Y496 (300 mg, 1.3 mmol) was dissolved in DMF (14 ml), methyl iodide (1 ml) and sodium hydride (316 mg, 13.1 mmol) were added, and the mixture was stirred at room temperature for 3 hr. Thereafter, water was carefully added until air bubbles ceased to occur, and the mixture was extracted twice with ethyl acetate. The organic layer was washed twice with saturated aqueous NaCl. The organic layer was dried over Na₂CO₃, the solvent was evaporated, and the obtained residue was purified by silica gel chromatography (eluent; hexane:ethyl acetate (4:1). The obtained compound was dissolved in ethyl acetate (10 ml), Pd/C (111 mg) was added, and the mixture was stirred under a hydrogen atmosphere at room temperature overnight. Then, the reaction solution was filtered through celite, the filtrate was concentrated under reduced pressure, and the obtained residue was purified by silica gel chromatography (eluent; chloroform) to give compound Y503 (yield (2 steps); 210 mg, 80%). Compound Y491 (mentioned later) (420 mg, 0.92 mmol) was dissolved in dichloromethane (10 ml), compound Y503 (210 mg, 1.0 mmol) and triethylamine (250 μl, 1.8 mmol) were added, and the mixture was stirred at room temperature for 3 hr. Then, the solvent was concentrated under reduced pressure, and the obtained residue was purified by silica gel chromatography (eluent; chloroform:methanol (40:1)) to give the title compound Y244 (yield; 309 mg, 100%).

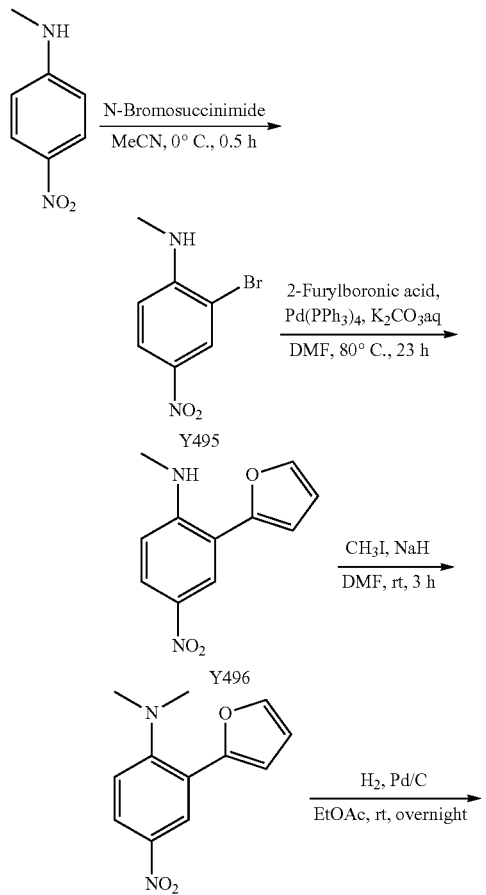

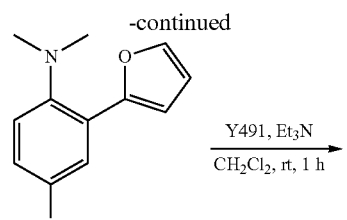

Y503

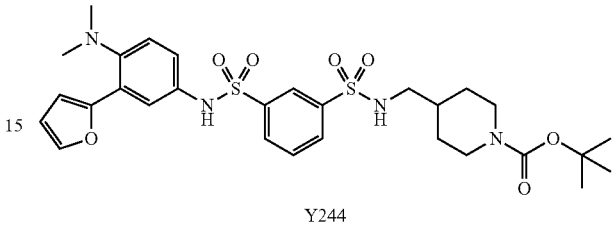

Y244

$^1$H NMR (500 MHz, CDCl₃) δ8.36 (s, 1H), 8.00 (d, 1H, J=7.0 Hz), 7.86 (d, 1H, J=8.5 Hz), 7.57 (dd, 1H, J=8.5, 7.0 Hz), 7.43-7.41 (m, 2H), 7.01-6.96 (m, 3H), 6.93 (bs, 1H), 6.47-6.46 (m, 1H), 4.92 (dd, 1H, J=7.0, 6.0 Hz), 4.07 (bs, 2H), 2.77-2.73 (m, 2H), 2.64 (s, 6H), 1.61-1.56 (m, 3H), 1.44 (s, 9H), 1.04-1.01 (m, 2H)

$^{13}$C NMR (125 MHz, CDCl₃) δ154.9, 141.6, 141.6, 140.9, 131.3, 131.1, 130.0, 125.9, 125.5, 123.1, 122.5, 111.9, 109.8, 79.7, 48.7, 44.1, 36.6, 29.6, 28.6

HRMS (FAB-) m/z: [M-H]⁻ calcd for C₂₉H₃₇N₄O₇S₂, 617.2104. found, 617.2101

Example 6

4-{[3-(3-furan-2-yl-4-piperidin-1-yl-phenylsulfamoyl)benzenesulfonylamino]methyl}piperidine-1-carboxylic acid tert-butyl ester (Y250)

2-Bromo-1-fluoro-4-nitrobenzene (2.0 g, 9.1 mmol) was dissolved in DMSO (20 ml), potassium carbonate (2.5 g, 18 mmol) and piperidine (1.8 ml, 18 mmol) were added, and the mixture was stirred at 90° C. overnight. Then, water was added to the reaction solution, and the mixture was extracted twice with ethyl acetate. The organic layer was washed twice with saturated aqueous NaCl. The organic layer was dried over Na₂CO₃, the solvent was evaporated, and the obtained residue was purified by silica gel chromatography (eluent; hexane:ethyl acetate (25:1) to give compound Y245 (yield; 2.52 g, 98%). Compound Y245 (334 mg, 1.2 mmol) was dissolved in DMF (12 ml), 2-furylboronic acid (201 mg, 1.8 mmol), Pd(PPh₃)₄ (416 mg, 30 mol %) and 2M Na₂CO₃ (1.7 ml) were added under a nitrogen stream, and the mixture was stirred under a nitrogen stream at 90° C. for 12.5 hr. Then, water was added to the reaction solution, and the mixture was extracted twice with ethyl acetate. The organic layer was washed twice with saturated aqueous NaCl. The organic layer was dried over Na₂CO₃, the solvent was evaporated, and the obtained residue was purified by silica gel chromatography (eluent; hexane:ethyl acetate (15:1) to give compound Y247 (yield; 313 mg, 96%). Compound Y247 (310 mg, 1.1 mmol) was dissolved in dichloromethane (13 ml), Pd/C (98 mg) was added, and the mixture was stirred under a hydrogen atmosphere at room temperature overnight. Then, the reaction solution was filtered through celite, the filtrate was concentrated under reduced pressure, and the obtained residue was purified by silica gel chromatography (eluent; chloroform) to give compound Y247a (yield; 271 mg, 91%). Compound Y247a was dissolved in dichloromethane (12 ml), compound Y491 (mentioned later) (151 mg, 0.33 mmol) and triethylamine (100 μl, 0.72 mmol) were added, and the mixture was stirred at room temperature for 5 hr. Then, the solvent was concentrated under reduced pressure, and the obtained residue was purified by silica gel chromatography (eluent; chloroform:methanol (40:1)) to give the title compound (yield; quantitative, 161 mg).

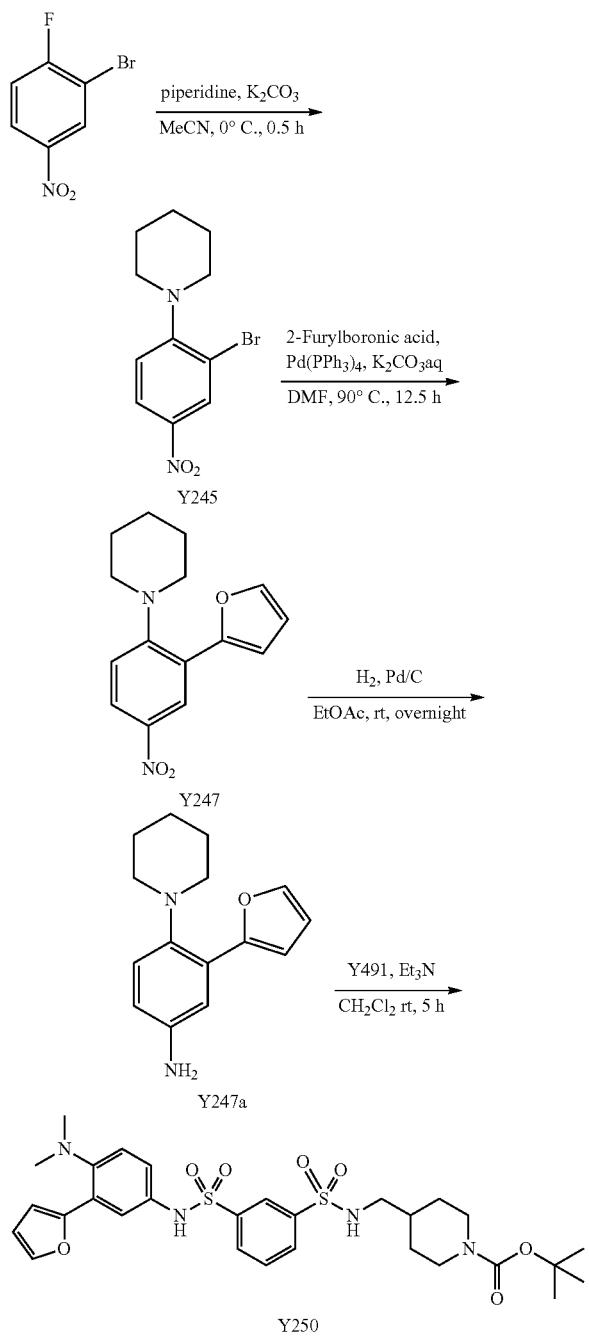

$^1$H NMR (500 MHz, CDCl$_3$) δ8.44 (s, 1H), 8.00 (d, 1H, J=8.0 Hz), 7.84 (d, 1H, J=8.0 Hz), 7.54 (t, 1H, J=8.0 Hz), 7.50 (d, 1H, J=2.0 Hz), 7.39 (bs, 2H), 7.21 (d, 1H, J=3.5 Hz), 7.02-6.97 (m, 2H), 6.45 (dd, 1H, J=3.5, 2.0 Hz), 5.31 (bs, 1H), 4.01 (bs, 2H), 2.78-2.61 (m, 8H), 1.68-1.54 (m, 9H), 1.43 (s, 9H), 1.06-0.98 (m, 2H)

$^{13}$C NMR (125 MHz, CDCl$_3$) δ155.0, 151.1, 149.3, 141.6, 141.5, 140.9, 131.3, 131.1, 130.9, 126.3, 125.8, 122.9, 121.8, 121.1, 111.9, 109.5, 79.8, 79.7, 77.4, 53.6, 48.6, 36.6, 31.1, 29.6, 28.6, 26.5, 24.2

HRMS (FAB-) m/z: [M-H]$^-$ calcd for C$_{32}$H$_{41}$N$_4$O$_7$S$_2$, 657.2417. found, 657.2433

Reference Example 1

Synthesis of Y491

1,3-Benzenedisulfonylchloride (1.3 g, 4.7 mmol) was dissolved in dichloromethane (25 ml), a solution (25 ml) of 1-Boc-4-(aminomethyl)piperidine (0.7 ml, 2.8 mmol) in dichloromethane was added under ice-cooling, and the mixture was stirred for 20 min. The reaction solvent was evaporated, and the obtained residue was purified by silica gel chromatography (eluent; chloroform:methanol (48:1)) to give the title compound Y491 (yield; 334 mg, 16%).

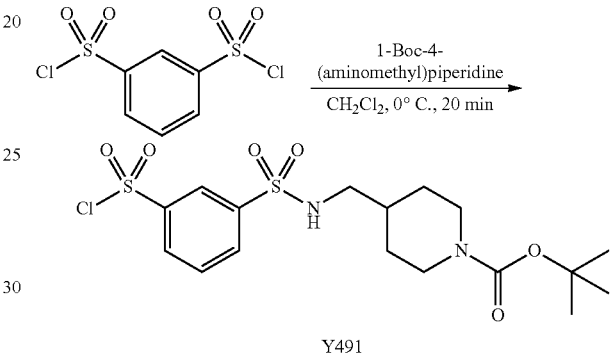

$^1$H NMR (500 MHz, CDCl$_3$) δ8.49 (s, 1H), 8.23-8.20 (m, 2H), 7.81 (dd, 1H, J=8.0, 7.0 Hz), 5.29 (t, 1H, J=6.5 Hz), 4.09-4.07 (m, 2H), 2.90 (dd, 2H, J=7.0, 6.0 Hz), 2.66-2.61 (m, 2H), 1.67-1.64 (m, 3H), 1.43 (s, 9H), 1.09-1.06 (m, 2H)

$^{13}$C NMR (125 MHz, CDCl$_3$) δ154.7, 145.2, 142.8, 133.1, 130.9, 130.4, 125.4, 79.6, 48.7, 48.6, 43.4, 36.5, 29.4, 28.4

HRMS (FAB-) m/z: [M-H]$^-$ calcd for C$_{17}$H$_{24}$ClN$_2$O$_6$S$_2$, 451.0764. found, 451.0753

Example 7

4-[3-(piperidine-1-sulfonyl)benzenesulfonyl]piperazine-1-carboxylic acid tert-butyl ester (Y043)

According to the final step (step for condensing Y222 and Y491) in Example 2, 1-(tert-butoxycarbonyl)piperazine and Y491 were condensed to give the title compound.

$^1$H NMR (500 MHz, CDCl$_3$) δ8.10 (s, 1H), 7.98 (d, 1H, J=8.0 Hz), 7.95 (d, 1H, J=8.0 Hz), 7.73 (dd, 1H, J=8.5, 8.0 Hz), 3.52-3.50 (m, 4H), 3.03-2.99 (m, 8H), 1.67-1.62 (m, 4H), 1.46-1.43 (m, 2H), 1.40 (s, 9H)

$^{13}$C NMR (125 MHz, CDCl$_3$) δ154.2, 138.8, 137.6, 131.8, 131.4, 130.3, 126.8, 80.8, 47.1, 46.1, 28.3, 25.3, 23.5

HRMS (FAB-) m/z: [M-H]$^-$ calcd for C$_{20}$H$_{30}$N$_3$O$_6$S$_2$, 472.1576. found, 472.1510

Example 8

4-{[3-(piperidine-1-sulfonyl)benzenesulfonylamino]-methyl}-s piperidine-1-carboxylic acid benzyl ester (Y053)

4-{[3-(Piperidine-1-sulfonyl)benzenesulfonylamino]methyl}piperidine-1-carboxylic acid tert-butyl ester (Y029) (1.16 g, 2.3 mmol) obtained in the below-mentioned Example 11 was dissolved in chloroform (15 ml), TFA (10 ml) was added under ice-cooling, and the mixture was stirred for 2 hr. The solvent was evaporated to give Y055 (yield; quantitative, 1.25 g). Y055 (148 mg, 0.37 mmol) was dissolved in chloroform (8 ml), triethylamine (153 ml, 1.1 mmol) and benzyloxycarbonyl chloride (157 ml, 1.1 mmol) were added under ice-cooling, and the mixture was stirred for 1 hr. Then, the solvent was concentrated under reduced pressure, and the obtained residue was purified by silica gel chromatography (eluent; chloroform:methanol (15:1)) to give the title compound (yield; 59 mg, 20%).

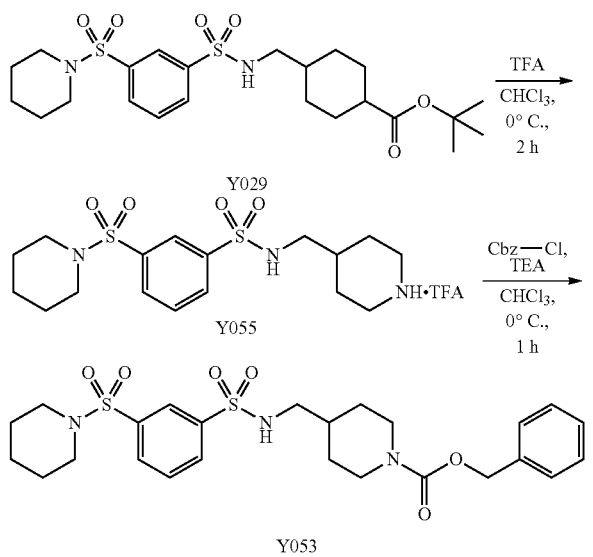

$^1$H NMR (500 MHz, CDCl$_3$) δ8.22 (dd, 1H, J=2.0, 1.5 Hz), 8.06 (ddd, 1H, J=8.0, 3.0, 1.5 Hz), 7.94 (ddd, 1H, J=8.0, 3.0, 1.5 Hz), 7.70 (t, 1H, J=8.0 Hz) 7.37-7.29 (m, 5H), 5.10 (s, 2H), 4.96 (bs, 1H), 4.17 (bs, 2H), 3.03-2.72 (m, 8H), 1.68-1.60 (m, 7H), 1.46-1.41 (m, 2H), 1.13-1.06 (m, 2H)

$^{13}$C NMR (125 MHz, CDCl$_3$) δ155.4, 141.9, 138.5, 136.9, 131.5, 130.8, 130.3, 128.7, 128.2, 128.0, 128.0, 126.2, 67.3, 48.7, 47.1, 43.8, 36.6, 29.6, 25.3, 23.5

HRMS (FAB-) m/z: [M-H]$^-$ calcd for C$_{25}$H$_{32}$N$_3$O$_6$S$_2$, 534.1733. found, 534.1760

Example 9

4-({methyl-[3-(methyl-p-tolylsulfamoyl)benzenesulfonyl]amino}methyl)piperidine-1-carboxylic acid tert-butyl ester (Y191)

4-[(3-p-Tolylsulfamoylbenzenesulfonylamino)methyl]piperidine-1-carboxylic acid tert-butyl ester (Y155) (235 mg, 0.45 mmol) obtained in the below-mentioned Example 21 was dissolved in THF (5 ml), methyl iodide (140 μl, 2.2 mmol) was added, sodium hydride (108 mg, 4.5 mmol) was carefully added, and the mixture was stirred at room temperature for 3 hr. Then, water was added to the reaction solution, and the mixture was extracted twice with chloroform. The organic layer was washed twice with saturated aqueous NaCl, and dried over Na$_2$CO$_3$. The solvent was evaporated, and the obtained residue was purified by silica gel chromatography (eluent; chloroform) to give the title compound (yield; 222 mg, 90%).

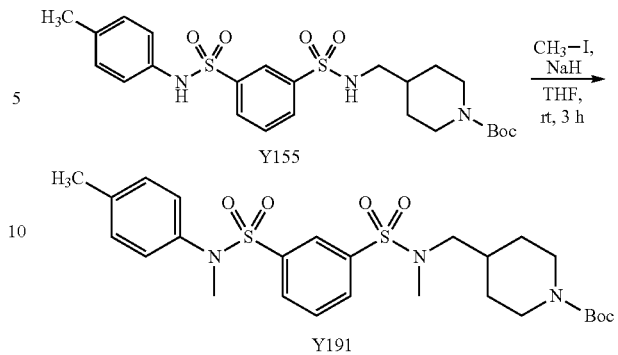

$^1$H NMR (500 MHz, CDCl$_3$) δ7.96-7.94 (m, 2H), 7.71-7.69 (m, 1H), 7.62 (dd, 1H, J=8.0, 7.5 Hz), 7.09 (d, 2H, J=8.0 Hz), 6.92 (d, 2H, J=8.5 Hz), 4.09 (d, 2H, J=12.5 Hz), 3.16 (s, 3H), 2.79 (d, 2H, J=6.0 Hz), 2.67 (s, 3H), 2.30 (s, 3H), 1.74-1.65 (m, 3H), 1.43 (s, 9H), 1.14-1.06 (m, 2H)

$^{13}$C NMR (125 MHz, CDCl$_3$) δ154.8, 139.1, 138.3, 138.3, 137.9, 131.5, 131.2, 129.9, 129.9, 126.5, 126.4, 79.5, 55.8, 43.5, 38.6, 35.7, 34.8, 29.7, 28.5, 21.1

HRMS (FAB-) m/z: [M-H]$^-$ calcd for C$_{26}$H$_{36}$N$_3$O$_6$S$_2$, 550.2046. found, 550.2113

Example 10

4-[({3-[(4-tert-butylphenyl)methylsulfamoyl]benzenesulfonyl}methylamino)-methyl]piperidine-1-carboxylic acid tert-butyl ester (Y205)

According to the final step (methylation of Y155) of Example 9, Y177 obtained in the below-mentioned Example 22 was contacted with methyl iodide to give the title compound.

$^1$H NMR (500 MHz, CDCl$_3$) δ7.97-7.95 (m, 2H), 7.74-7.72 (m, 1H), 7.63 (dd, 1H, J=8.0, 7.5 Hz), 7.31 (dd, 2H, J=8.5, 2.5 Hz), 6.98 (dd, 2H, J=8.5, 2.5 Hz), 4.11 (d, 2H, J=13.0 Hz), 3.19 (s, 3H), 2.82 (d, 2H, J=6.5 Hz), 2.69 (s, 3H), 1.75-1.67 (m, 3H), 1.45 (s, 9H), 1.29 (s, 9H), 1.17-1.08 (m, 2H)

$^{13}$C NMR (125 MHz, CDCl$_3$) δ154.9, 151.2, 139.2, 138.6, 138.2, 131.6, 131.2, 130.0, 126.6, 126.3, 79.6, 55.9, 43.6, 38.6, 35.9, 34.9, 34.8, 34.7, 31.4, 29.8, 28.6

HRMS (FAB-) m/z: [M-H]$^-$ calcd for C$_{29}$H$_{42}$N$_3$O$_6$S$_2$, 592.2515. found, 550.2534

Example 11

4-{[3-(piperidine-1-sulfonyl)benzenesulfonylamino]methyl}piperidine-1-carboxylic acid tert-butyl ester (Y029)

According to the final step (step for condensing Y222 and Y491) in Example 2, piperidine and Y491 were condensed to give the title compound.

$^1$H NMR (500 MHz, CDCl$_3$) δ8.22 (s, 1H), 8.06 (d, 1H, J=8.0 Hz), 7.95 (d, 1H, J=8.0 Hz), 7.70 (t, 1H, J=8.0 Hz), 4.92 (dd, 1H, J=6.5, 6.0 Hz), 4.08 (bs, 2H), 3.03-3.01 (m, 4H), 2.85 (dd, 2H, J=6.5, 6.0 Hz), 2.63 (m, 2H), 1.67-1.56 (m, 8H), 1.43 (s, 9H), 1.10-1.02 (m, 2H)

$^{13}$C NMR (125 MHz, CDCl$_3$) δ154.9, 141.9, 138.5, 131.4, 130.8, 130.3, 126.1, 88.7, 79.8, 48.8, 47.1, 36.7, 34.5, 29.7, 28.6, 25.2, 23.5

HRMS (FAB-) m/z: [M-H]⁻ calcd for $C_{22}H_{34}N_3O_6S_2$, 500.1889. found, 500.1955

Example 12

4-[(3-diethylsulfamoylbenzenesulfonylamino)methyl]piperidine-1-carboxylic acid tert-butyl ester (Y080)

According to the final step (step for condensing Y222 and Y491) in Example 2, diethylamine and Y491 were condensed to give the title compound.

$^1$H NMR (500 MHz, CDCl$_3$) δ 8.27 (dd, 1H, J=2.0, 1.5 Hz), 8.03-7.98 (m, 2H), 7.66 (dd, 1H, J=8.0, 7.5 Hz), 5.18 (dd, 1H, J=6.0, 7.0 Hz), 4.05 (bs, 2H), 3.26 (dd, 4H, J=14.0, 7.5 Hz), 2.82 (dd, 2H, J=6.5, 6.0 Hz), 2.6 (bs, 2H), 1.64-1.58 (m, 3H), 1.42 (s, 9H), 1.13 (dd, 6H, J=14.5, 7.5 Hz), 1.08-0.99 (m, 2H)

$^{13}$C NMR (125 MHz, CDCl$_3$) δ 154.9, 142.2, 141.9, 130.7, 130.5, 130.3, 125.6, 79.7, 48.8, 42.4, 36.6, 29.6, 28.6, 14.3

HRMS m/z: [M-H]⁻ calcd for $C_{21}H_{35}N_3O_6S_2$, 488.1889. found, 488.1898

Example 13

4-{[3-(morpholine-4-sulfonyl)benzenesulfonylamino]methyl}piperidine-1-carboxylic acid tert-butyl ester (Y081)

According to the final step (step for condensing Y222 and Y491) in Example 2, morpholine and Y491 were condensed to give the title compound.

$^1$H NMR (500 MHz, CDCl$_3$) δ 8.22 (m, 1H), 8.09 (dd, 1H, J=8.0, 1.0 Hz), 7.94 (dd, 1H, J=8.0, 1.0 Hz), 7.73 (dd, 1H, J=8.0, 7.5 Hz), 5.23-5.20 (m, 1H), 4.06 (m, 2H), 3.75-3.73 (m, 4H), 3.04-3.02 (m, 4H), 2.85 (dd, 2H, J=6.5, 6.0 Hz), 2.63 (m, 2H), 1.65-1.60 (m, 3H), 1.42 (s, 9H), 1.10-1.01 (m, 2H)

$^{13}$C NMR (125 MHz, CDCl$_3$) δ 154.9, 142.2, 137.2, 137.2, 131.5, 131.3, 130.4, 126.3, 79.7, 66.2, 48.8, 46.1, 36.7, 29.6, 28.6

HRMS (FAB-) m/z: [M-H]⁻ calcd for $C_{21}H_{32}N_3O_7S_2$, 502.1682. found, 502.1683

Example 14

4-[(3-sulfamoylbenzenesulfonylamino)methyl]piperidine-1-carboxylic acid tert-butyl ester (Y082)

According to the final step (step for condensing Y222 and Y491) in Example 2 and using aqueous ammonia, aqueous ammonia and Y491 were condensed to give the title compound.

$^1$H NMR (500 MHz, CDCl$_3$) δ 8.39 (s, 1H), 8.06 (d, 1H, J=8.0 Hz), 7.97 (d, 1H, J=7.5 Hz), 7.62 (dd, 1H, J=8.0, 7.5 Hz), 6.07 (bs, 2H), 5.97 (dd, 1H, J=6.5, 6.0 Hz), 3.94 (d, 2H, J=12.5 Hz), 2.78-2.45 (m, 4H), 1.59-1.57 (m, 3H), 1.37 (s, 9H), 0.97 (m, 2H)

$^{13}$C NMR (125 MHz, CDCl$_3$) δ 155.1, 143.9, 141.4, 130.8, 130.4, 130.3, 125.0, 79.9, 77.5, 48.6, 36.3, 29.5, 28.6

HRMS (FAB-) m/z: [M-H]⁻ calcd for $C_{17}H_{26}N_3O_6S_2$, 432.1263. found, 432.1405

Example 15

4-(benzenesulfonylaminomethyl)piperidine-1-carboxylic acid tert-butyl ester (Y083)

According to Reference Example 1, benzenesulfonylchloride and 1-Boc-4-(aminomethyl)piperidine were condensed to give the title compound.

$^1$H NMR (500 MHz, CDCl$_3$) δ 7.83-7.81 (m, 2H), 7.55-7.45 (m, 3H), 5.55 (t, 1H, J=6.0 Hz), 4.00 (d, 2H, J=12.0 Hz), 2.75 (dd, 2H, J=7.0, 6.0 Hz), 2.56 (t, 2H, J=12.5 Hz), 1.61-1.51 (m, 3H), 1.38 (s, 9H), 1.02-0.94 (m, 2H)

$^{13}$C NMR (125 MHz, CDCl$_3$) δ 154.8, 140.1, 132.7, 129.2, 127.0, 79.5, 77.4, 50.6, 48.6, 36.4, 29.6, 28.5

HRMS (FAB-) m/z: [M-H]⁻ calcd for $C_{17}H_{25}N_2O_4S$, 353.1535. found, 353.1549

Example 16

4-{[3-(cyclohexylmethylsulfamoyl)benzenesulfonylamino]methyl}-piperidine-1-carboxylic acid tert-butyl ester (Y101)

According to the final step (step for condensing Y222 and Y491) in Example 2, aminomethylcyclohexane and Y491 were condensed to give the title compound.

$^1$H NMR (500 MHz, CDCl$_3$) δ 8.40 (dd, 1H, J=2.0, 1.5 Hz), 8.04 (ddd, 2H, J=8.0, 2.0, 1.5 Hz), 7.68 (t, 1H, J=8.0 Hz), 5.50 (dd, 1H, J=6.5, 6.0 Hz), 5.33 (dd, 1H, J=6.5, 6.0 Hz), 4.05 (bs, 1H), 2.83-2.77 (m, 4H), 2.63 (bs, 2H), 1.67-1.57 (m, 9H), 1.43 (s, 9H), 1.21-1.01 (m, 4H), 0.88-0.81 (m, 2H)

$^{13}$C NMR (125 MHz, CDCl$_3$) δ 154.9, 142.1, 141.8, 130.9, 130.8, 130.1, 125.6, 79.7, 49.6, 48.7, 37.9, 36.6, 30.6, 29.6, 28.6, 26.3, 25.8

HRMS (FAB-) m/z: [M-H]⁻ calcd for $C_{24}H_{38}N_3O_6S_2$, 528.2202. found, 528.2215

Example 17

4-[(3-phenylsulfamoylbenzenesulfonylamino)methyl]piperidine-1-carboxylic acid tert-butyl ester (Y098)

According to the final step (step for condensing Y222 and Y491) in Example 2, aniline and Y491 were condensed to give the title compound.

$^1$H NMR (500 MHz, CDCl$_3$) δ 8.50 (s, 1H), 8.03 (d, 1H, J=8.0 Hz), 7.83 (d, 1H, J=8.0 Hz), 7.79 (s, 1H), 7.57 (t, 1H, J=8.0 Hz), 7.26-2.14 (m, 5H), 5.59 (dd, 1H, J=7.0, 6.5 Hz), 4.07 (bs, 2H), 2.80-2.64 (m, 4H), 1.65-1.58 (m, 3H), 1.46 (s, 9H), 1.10-1.02 (m, 2H)

$^{13}$C NMR (125 MHz, CDCl$_3$) δ 154.9, 141.6, 140.7, 136.1, 131.2, 130.0, 129.6, 125.8, 122.5, 79.8, 48.7, 36.5, 29.6, 28.6

HRMS (FAB-) m/z: [M-H]⁻ calcd for $C_{23}H_{30}N_3O_6S_2$, 508.1576. found, 508.1599

Example 18

4-{[3-(4-methoxyphenylsulfamoyl)benzenesulfonylamino]methyl}piperidine-1-carboxylic acid tert-butyl ester (Y141)

According to the final step (step for condensing Y222 and Y491) in Example 2, p-anisidine and Y491 were condensed to give the title compound.

$^1$H NMR (500 MHz, CDCl$_3$) δ 8.43 (s, 1H), 7.99 (d, 1H, J=8.0 Hz), 7.70 (d, 1H, J=8.0 Hz), 7.52 (t, 1H, J=8.0 Hz), 6.99 (d, 2H, J=9.0 Hz), 6.74 (d, 2H, J=9.0 Hz), 5.72 (dd, 1H, J=6.5, 6.0 Hz), 4.03 (bs, 2H), 3.73 (s, 3H), 2.76-2.61 (m, 4H), 1.63-1.54 (m, 3H), 1.41 (s, 9H), 1.07-1.00 (m, 2H)

$^{13}$C NMR (125 MHz, CDCl$_3$) δ 158.4, 155.0, 141.5, 140.6, 131.3, 131.1, 129.9, 125.8, 116.8, 115.0, 114.7, 79.8, 77.5, 55.9, 55.6, 48.6, 36.5, 29.6, 28.6

HRMS (FAB-) m/z: [M-H]⁻ calcd for $C_{24}H_{32}N_3O_7S_2$, 538.1682. found, 538.1633

Example 19

4-{[3-(3-methoxyphenylsulfamoyl)benzenesulfonylamino]methyl}piperidine-1-carboxylic acid tert-butyl ester (Y142)

According to the final step (step for condensing Y222 and Y491) in Example 2, m-anisidine and Y491 were condensed to give the title compound.

¹H NMR (500 MHz, CDCl₃) δ8.44 (s, 1H), 7 (d, 1H, J=8.0 Hz), 7.86 (d, 1H, J=8.0 Hz), 7.54 (t, 1H, J=8.0 Hz), 7.08 (t, 1H, J=8.0 Hz), 6.72 (dd, 1H, J=2.5, 2.0 Hz), 6.68-6.62 (m, 2H), 5.73 (dd, 1H, J=6.5, 6.0 Hz), 4.02 (bs, 2H), 3.70 (s, 3H), 2.72 (t, 2H, J=6.5 Hz), 2.60 (bs, 2H), 1.60-1.54 (m, 3H), 1.42 (s, 9H), 1.05-0.97 (m, 2H)

¹³C NMR (125 MHz, CDCl₃) δ160.4, 154.9, 147.8, 141.5, 140.6, 137.4, 131.2, 130.3, 130.2, 125.8, 114.0, 111.4, 107.8, 79.8, 55.4, 55.2, 48.6, 36.4, 29.5, 28.6

HRMS (FAB-) m/z: [M-H]⁻ calcd for $C_{24}H_{32}N_3O_7S_2$, 538.1682. found, 538.1674

Example 20

4-{[3-(2-methoxyphenylsulfamoyl)benzenesulfonylamino]methyl}piperidine-1-carboxylic acid tert-butyl ester (Y140)

According to the final step (step for condensing Y222 and Y491) in Example 2, o-anisidine and Y491 were condensed to give the title compound.

¹H NMR (500 MHz, CDCl₃) δ8.28 (s, 1H), 7.96 (d, 1H, J=8.0 Hz), 7.85 (d, 1H, J=8.0 Hz), 7.52 (t, 1H, J=8.0 Hz), 7.50 (dd, 1H, J=8.0, 1.5 Hz), 7.07 (ddd, 1H, J=9.5, 8.0, 1.5 Hz), 6.90 (ddd, 1H, J=8.0, 7.5, 1.0 Hz), 6.70 (d, 1H, J=7.5 Hz), 5.36 (dd, 1H, J=7.0, 6.0 Hz), 4.04 (bs, 2H), 3.57 (s, 3H), 2.73-2.60 (m, 4H), 1.62-1.52 (m, 3H), 1.42 (s, 9H), 1.04-0.97 (m, 2H)

¹³C NMR (125 MHz, CDCl₃) δ154.9, 150.4, 141.5, 140.7, 131.1, 131.0, 129.8, 126.8, 125.9, 124.9, 123.0, 121.2, 110.9, 100.0, 79.7, 55.7, 48.6, 36.5, 29.5, 28.5

HRMS (FAB-) m/z: [M-H]⁻ calcd for $C_{24}H_{32}N_3O_7S_2$, 538.1682. found, 538.1657

Example 21

4-[(3-p-tolylsulfamoylbenzenesulfonylamino)methyl]piperidine-1-carboxylic acid tert-butyl ester (Y155)

According to the final step (step for condensing Y222 and Y491) in Example 2, 1-amino-4-methylbenzene and Y491 were condensed to give the title compound.

¹H NMR (500 MHz, CDCl₃) δ8.47 (s, 1H), 8.01 (d, 1H, J=8.0 Hz), 7.75 (d, 1H, J=8.0 Hz), 7.55-7.51 (m, 2H), 7.04-6.98 (m, 4H), 5.49 (dd, 1H, J=7.0, 6.5 Hz), 4.05 (bs, 2H), 2.87-2.62 (m, 4H), 2.27 (s, 3H), 1.64-1.56 (m, 3H), 1.43 (s, 9H), 1.08-1.00 (m, 2H)

¹³C NMR (125 MHz, CDCl₃) δ155.0, 141.6, 140.7, 136.3, 133.2, 131.3, 130.2, 130.0, 129.9, 125.8, 123.2, 79.7, 48.7, 36.5, 28.6, 21.1

HRMS (FAB-) m/z: [M-H]⁻ calcd for $C_{24}H_{32}N_3O_6S_2$, 522.1733. found, 522.1766

Example 22

4-{[3-(4-tert-butylphenylsulfamoyl)benzenesulfonylamino]methyl}piperidine-1-carboxylic acid tert-butyl ester (Y177)

According to the final step (step for condensing Y222 and Y491) in Example 2, tert-butylaniline and Y491 were condensed to give the title compound.

¹H NMR (500 MHz, CDCl₃) δ8.47 (s, 1H), 8.00 (d, 1H, J=8.0 Hz), 7.80 (d, 1H, J=8.0 Hz), 7.56 (t, 1H, J=8.0 Hz), 7.44 (s, 1H), 7.25 (d, 2H, J=8.5 Hz), 7.03 (d, 2H, J=8.5 Hz), 5.41 (t, 1H, J=6.5 Hz), 4.06 (bs, 2H), 2.81 (dd, 2H, J=6.5, 6.0 Hz), 2.63 (bs, 2H), 1.65-1.56 (m, 3H), 1.43 (s, 9H), 1.26 (s, 9H), 1.10-1.02 (m, 2H)

¹³C NMR (125 MHz, CDCl₃) δ155.0, 149.5, 141.7, 141.0, 133.2, 131.3, 131.1, 130.0, 126.5, 125.9, 122.6, 79.6, 48.8, 36.6, 34.6, 31.2, 31.4, 29.7, 28.6

HRMS (FAB-) m/z: [M-H]⁻ calcd for $C_{27}H_{38}N_3O_6S_2$, 564.2202. found, 564.2215

Example 23

4-{[3-(4-dimethylaminophenylsulfamoyl)benzenesulfonylamino]methyl}-piperidine-1-carboxylic acid tert-butyl ester (Y178)

According to the final step (step for condensing Y222 and Y491) in Example 2, 4-(dimethylamine)aniline and Y491 were condensed to give the title compound.

¹H NMR (500 MHz, CDCl₃) δ8.39 (s, 1H), 8.00 (d, 1H, J=8.0 Hz), 7.70 (d, 1H, J=8.0 Hz), 7.54 (t, 1H, J=8.0 Hz), 6.92-6.89 (m, 3H), 6.55 (d, 2H, J=9.0 Hz), 5.23 (dd, 1H, J=6.5, 6.0 Hz), 4.07 (bs, 2H), 2.90 (s, 6H), 2.78 (dd, 2H, J=6.5, 6.0 Hz), 2.64 (bs, 2H), 1.66-1.56 (m, 3H), 1.44 (s, 9H), 1.10-1.01 (m, 2H)

¹³C NMR (125 MHz, CDCl₃) δ155.0, 149.8, 141.5, 141.0, 131.4, 130.0, 129.8, 126.6, 125.9, 123.9, 112.8, 79.7, 77.4, 48.8, 40.7, 36.6, 29.7, 28.6

HRMS (FAB-) m/z: [M-H]⁻ calcd for $C_{25}H_{35}N_3O_6S_2$, 551.1998. found, 551.1984

Example 24

4-{[3-(4-acetylphenylsulfamoyl)benzenesulfonylamino]methyl}piperidine-1-carboxylic acid tert-butyl ester (Y192)

According to the final step (step for condensing Y222 and Y491) in Example 2, 1-acetyl-4-aminobenzene and Y491 were condensed to give the title compound.

¹H NMR (500 MHz, CDCl₃) δ8.44 (s, 1H), 8.02 (d, 1H, J=8.0 Hz), 7.87 (d, 1H, J=8.0 Hz), 7.73-7.67 (m, 3H), 7.59 (t, 1H, J=8.0 Hz), 7.42-7.37 (m, 2H), 5.33 (t, 1H, J=6.5 Hz), 4.07 (d, 2H, J=13.5 Hz), 2.83-2.80 (m, 2H), 2.68-2.59 (m, 2H), 2.56 (s, 3H), 1.64-1.56 (m, 3H), 1.44 (s, 9H), 1.10-1.02 (m, 2H)

¹³C NMR (125 MHz, CDCl₃) δ197.6, 155.0, 148.6, 148.5, 142.0, 140.7, 138.4, 136.8, 131.4, 131.1, 130.2, 126.7, 126.1, 126.0, 125.9, 121.5, 79.8, 48.7, 36.6, 29.6, 28.6, 26.9

HRMS (FAB-) m/z: [M-H]⁻ calcd for $C_{25}H_{32}N_3O_7S_2$, 550.1682. found, 550.1649

Example 25

4-({3-[4-(1-hydroxyethyl)phenylsulfamoyl]benzenesulfonylamino}methyl)-piperidine-1-carboxylic acid tert-butyl ester (Y195)

4-{[3-(4-Acetylphenylsulfamoyl)benzenesulfonylamino]methyl}piperidine-1-carboxylic acid tert-butyl ester obtained in Example 24 was reduced to give the title compound.

That is, 1-acetyl-aminobenzene (300 mg, 2.2 mmol) was dissolved in methanol, sodium borohydride (418 mg, 11 mmol) was added, the temperature was raised from under ice-cooling to room temperature, and the mixture was stirred for 1 hr. Then, water was added to the reaction mixture, and unreacted sodium borohydride was decomposed. Then, the solvent was evaporated under reduced pressure, and the obtained residue was purified by silica gel chromatography (eluent; chloroform:methanol (30:1)) to give 1-(aminophenyl)ethanol (yield; 242 mg, 80%). According to the final step in Example 2 (step for condensing Y222 and Y491), compound Y491 (the aforementioned) (196 mg, 4.3 mmol) and 1-(aminophenyl)ethanol (147 mg, 10.8 mmol) were condensed to give the title compound (yield; 157 mg, 66%).

$^1$H NMR (500 MHz, CDCl$_3$) δ8.26 (s, 1H), 7.97 (d, 1H, J=7.5 Hz), 7.87 (d, 1H, J=8.0 Hz), 7.54 (dd, 1H, J=8.0, 7.5 Hz), 7.21 (d, 2H, J=8.0 Hz), 7.03 (d, 2H, J=8.5 Hz), 5.80 (dd, 1H, J=6.5, 6.0 Hz), 4.78 (m, 1H), 3.97-3.94 (m, 2H), 2.75-2.55 (m, 4H), 1.65 (s, 3H), 1.53 (m, 3H), 1.41 (s, 9H), 0.97-0.95 (m, 2H)

$^{13}$C NMR (125 MHz, CDCl$_3$) δ155.0, 143.8, 141.7, 140.8, 135.2, 131.0, 130.0, 126.8, 125.7, 122.3, 79.9, 77.4, 69.6, 58.5, 50.8, 48.6, 36.4, 29.5, 28.6, 25.1, 18.5

HRMS (FAB-) m/z: [M-H]$^-$ calcd for C$_{25}$H$_{34}$N$_3$O$_7$S$_2$, 552.1838. found, 552.1830

Example 26

4-{[3-(4-hydroxyphenylsulfamoyl)benzenesulfonylamino]methyl}piperidine-1-carboxylic acid tert-butyl ester (Y196)

According to the final step (step for condensing Y222 and Y491) in Example 2, 4-hydroxyaniline and Y491 were condensed to give the title compound.

$^1$H NMR (500 MHz, CDCl$_3$) δ8.25 (s, 1H), 8.11 (d, 1H, J=7.5 Hz), 8.00 (d, 1H, J=8.0 Hz), 7.68 (t, 1H, J=8.0 Hz), 6.73 (d, 2H, J=8.5 Hz), 6.53 (d, 2H, J=9.0 Hz), 5.04 (t, 1H, J=6.5 Hz), 4.07 (s, 2H), 2.80-2.63 (m, 4H), 1.64-1.55 (m, 3H), 1.43 (s, 9H), 1.07-1.00 (m, 2H)

$^{13}$C NMR (125 MHz, CDCl$_3$) δ155.0, 145.8, 142.0, 141.4, 137.1, 132.3, 132.2, 130.3, 127.1, 123.2, 115.7, 79.8, 58.6, 51.6, 48.8, 36.6, 29.6, 28.6, 18.6

HRMS (FAB-) m/z: [M-H]$^-$ calcd for C$_{23}$H$_{30}$N$_3$O$_7$S$_2$, 524.1525. found, 524.1522

Example 27

4-{[3-(4-azidophenylsulfamoyl)benzenesulfonylamino]methyl}piperidine-1-carboxylic acid tert-butyl ester (Y241)

4-Nitroaniline (500 mg, 3.6 mmol) was dissolved in ethyl acetate (36 ml), Pd/C (171 mg) was added, and the mixture was stirred under a hydrogen atmosphere at room temperature overnight. Then, the reaction solution was filtered through celite, and the filtrate was concentrated under reduced pressure to give compound Y137 (yield; 386 mg, 99%). Y491 (274 mg, 0.6 mmol) was dissolved in dichloromethane (6 ml), Y137 (196 mg) was added, and the mixture was stirred at room temperature for 3 hr. Then, the solvent was evaporated, and the obtained residue was purified by silica gel chromatography (eluent; chloroform:methanol (30:1)) to give Y138 (yield; 279 mg, 89%). Y138 (279 mg, 0.53 mmol) was dissolved in 90% acetic acid (6 ml), sodium nitrite (183 mg, 2.7 mmol) was added under ice-cooling, and the mixture was stirred for 15 min. Then, sodium azide (173 mg, 2.7 mmol) was added, and the mixture was stirred for 1 hr. Then, the solvent was evaporated, and the obtained residue was purified by silica gel chromatography (eluent; chloroform:methanol (20:1)) to give the title compound (yield; 260 mg, 89%).

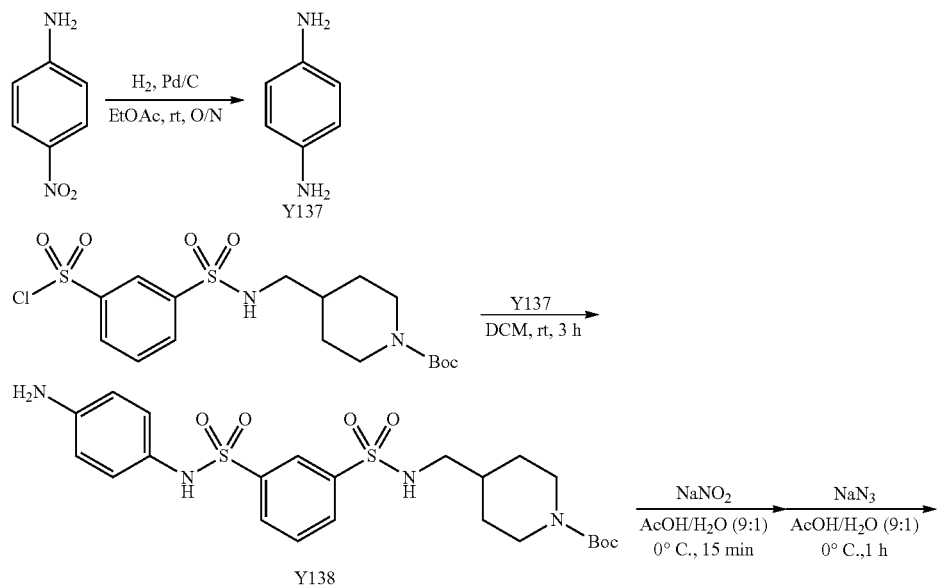

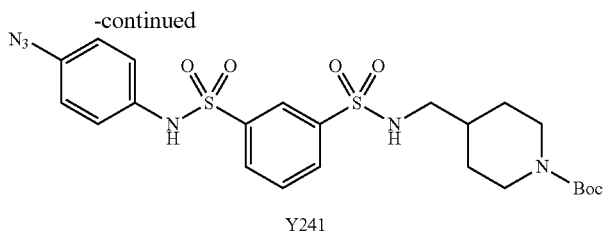

Y241

$^{1}$H NMR (500 MHz, CDCl$_{3}$) δ8.48 (s, 1H), 8.03 (d, 1H, J=8.0 Hz), 7.73 (d, 1H, J=8.0 Hz), 7.57 (t, 1H, J=8.0 Hz), 7.53 (s, 1H), 7.12 (dd, 2H, J=8.5, 1.5 Hz), 6.91 (dd, 2H, J=8.0, 1.5 Hz), 5.39 (t, 1H, J=6.5 Hz), 4.07 (d, 2H, J=14.0 Hz), 2.81 (dd, 2H, J=6.5, 6.5 Hz), 2.67-2.62 (m, 2H), 1.65-1.56 (m, 3H), 1.43 (s, 9H), 1.10-1.03 (m, 2H)

$^{13}$C NMR (125 MHz, CDCl$_{3}$) δ155.0, 141.8, 140.6, 138.6, 132.6, 131.3, 131.2, 130.1, 125.8, 124.9, 120.1, 79.8, 77.5, 48.8, 43.6, 36.6, 29.6, 28.6

HRMS (FAB-) m/z: [M-H]$^{-}$ calcd for C$_{23}$H$_{29}$N$_{6}$O$_{6}$S$_{2}$, 549.1590. found, 549.1592

Example 28

4-(4-{3-[(1-tert-butoxycarbonylpiperidin-4-ylmethyl)sulfamoyl]benzenesulfonylamino}phenyl)piperazine-1-carboxylic acid tert-butyl ester (Y260)

The same steps as in Example 2 except the use of 1-(tert-butoxycarbonyl)piperazine instead of piperidine were performed to give the title compound.

$^{1}$H NMR (500 MHz, CDCl$_{3}$) δ8.44 (s, 1H), 8.00 (d, 1H, J=8.5 Hz), 7.70 (d, 1H, J=8.0 Hz), 7.52 (dd, 1H, J=8.0, 7.5 Hz), 7.48 (s, 1H), 6.98 (d, 2H, J=9.0 Hz), 6.77 (d, 2H, J=9.0 Hz), 5.57 (dd, 1H, J=6.5, 6.0 Hz), 4.05 (bs, 2H), 3.55-3.53 (m, 4H), 3.08-3.06 (m, 4H), 2.80-2.63 (m, 4H), 1.64 (m, 3H), 1.46 (s, 9H), 1.42 (s, 9H), 1.08-1.01 (m, 2H)

$^{13}$C NMR (125 MHz, CDCl$_{3}$) δ155.0, 154.8, 141.6, 140.8, 131.3, 131.0, 129.8, 127.7, 80.2, 79.7, 49.3, 48.7, 36.5, 29.6, 28.6, 28.5

HRMS (FAB-) m/z: [M-H]$^{-}$ calcd for C$_{32}$H$_{46}$N$_{5}$O$_{8}$S$_{2}$, 692.2788. found, 692.2727

Example 29

4-{[3-(3-furan-2-yl-phenylsulfamoyl)benzenesulfonylamino]methyl}piperidine-1-carboxylic acid tert-butyl ester (Y284)

The same steps as the steps after the coupling reaction of Y245 and 2-furylboronic acid in Example 6 were performed using 3-bromo-nitrobenzene instead of Y245 to give the title compound.

$^{1}$H NMR (500 MHz, CDCl$_{3}$) δ8.41 (s, 1H), 8.01 (d, 1H, J=8.0 Hz), 7.89 (d, 1H, J=8.0 Hz), 7.58 (t, 1H, J=8.0 Hz), 7.47-7.44 (m, 3H), 7.21 (s, 1H), 7.01-6.99 (m, 1H), 6.64 (d, 1H, J=3.5 Hz), 6.46 (dd, 1H, J=3.5, 1.5 Hz), 4.97 (dd, 1H, J=7.0, 6.0 Hz), 4.06 (d, 2H, J=13.0 Hz), 2.74-2.59 (m, 4H), 1.60-1.55 (m, 3H), 1.45 (s, 9H), 1.05-0.98 (m, 2H)

$^{13}$C NMR (125 MHz, CDCl$_{3}$) δ155.0, 152.8, 142.8, 141.7, 140.7, 136.5, 132.6, 132.5, 132.4, 131.3, 131.2, 130.2, 125.9, 121.5, 120.9, 117.4, 112.1, 106.3, 79.8, 48.7, 36.6, 29.6, 28.7

HRMS (FAB-) m/z: [M-H]$^{-}$ calcd for C$_{32}$H$_{46}$N$_{5}$O$_{8}$S$_{2}$, 692.2788. found, 692.2727

Example 30

4-{[3-(3-thiophen-2-yl-phenylsulfamoyl)benzenesulfonylamino]methyl}piperidine-1-carboxylic acid tert-butyl ester (Y296)

The same steps as in Example 29 except the use of 2-thienylboronic acid instead of 2-furylboronic acid were performed to give the title compound.

$^{1}$H NMR (500 MHz, CDCl$_{3}$) δ8.48 (s, 1H), 8.00 (d, 1H, J=8.0 Hz), 7.88 (d, 1H, J=8.0 Hz), 7.56 (t, 1H, J=8.0 Hz), 7.39-7.35 (m, 2H), 7.26-7.22 (m, 3H), 7.06-7.03 (m, 2H), 5.40 (bs, 1H), 4.04 (m, 2H), 2.72-2.59 (m, 4H), 1.58-1.51 (m, 3H), 1.43 (s, 9H), 1.03-0.96 (m, 2H)

$^{13}$C NMR (125 MHz, CDCl$_{3}$) δ154.9, 143.2, 141.7, 140.7, 136.9, 135.9, 131.3, 130.2, 130.1, 128.4, 125.9, 125.7, 123.9, 123.5, 121.0, 119.3, 79.8, 48.7, 36.5, 29.6, 28.6

HRMS (FAB-) m/z: [M-H]$^{-}$ calcd for C$_{27}$H$_{32}$N$_{3}$O$_{6}$S$_{3}$, 590.1453. found, 590.1503

Example 31

4-({3-[4-(4-benzoylpiperazin-1-yl)phenylsulfamoyl]benzenesulfonylamino}methyl)piperidine-1-carboxylic acid tert-butyl ester (Y366)

According to the final step (step for condensing Y222 and Y491) in Example 2, (4-aminophenyl)-phenyl-methanone and Y491 were condensed to give the title compound.

HRMS (FAB-) m/z: [M-H]$^{-}$ calcd for C$_{30}$H$_{34}$N$_{3}$O$_{7}$S$_{2}$, 611.1838. found, 612.1848

Example 32

4-{[3-(4-oxanylmethoxyphenylsulfamoyl)benzenesulfonylamino]methyl}-piperidine-1-carboxylic acid tert-butyl ester (Y198)

According to the final step (step for condensing Y222 and Y491) in Example 2, benzeneamine 4-(2-oxyanylmethoxy) and Y491 were condensed to give the title compound.

$^{1}$H NMR (500 MHz, CDCl$_{3}$) δ8.40 (s, 1H), 8.01 (d, 1H, J=7.5 Hz), 7.72 (d, 1H, J=8.0 Hz), 7.54 (t, 1H, J=8.0 Hz), 7.34 (s, 1H), 7.00 (d, 2H, J=9.0 Hz), 6.78 (d, 2H, J=9.0 Hz), 5.42 (dd, 1H, J=6.5, 6.0 Hz), 4.19-4.04 (m, 3H), 3.87 (dd, 1H, J=9.0, 3.5 Hz), 3.76-3.73 (m, 2H), 2.77 (dd, 2H, J=6.5, 6.0 Hz), 2.64-2.60 (m, 2H), 1.63-1.56 (m, 3H), 1.43 (s, 9H), 1.07-1.00 (m, 2H)

$^{13}$C NMR (125 MHz, CDCl$_3$) δ157.5, 154.9, 141.6, 140.6, 131.3, 131.1, 129.9, 128.7, 125.9, 125.8, 115.4, 79.8, 77.4, 73.7, 66.3, 48.7, 43.6, 36.5, 29.6, 28.6, 19.0

Example 33

4-{[3-(4-trifluoromethylphenylsulfamoyl)benzenesulfonylamino]methyl}-piperidine-1-carboxylic acid tert-butyl ester (Y145)

According to the final step (step for condensing Y222 and Y491) in Example 2, 4-aminobenzotrifluoride and Y491 were condensed to give the title compound.
HRMS (FAB-) m/z: [M-H]$^-$ calcd for C$_{24}$H$_{29}$F$_3$N$_3$O$_6$S$_2$, 576.1450. found, 576.1463

Example 34

4-{[3-(2-acetylaminophenylsulfamoyl)benzenesulfonylamino]methyl}-piperidine-1-carboxylic acid tert-butyl ester (Y147)

According to the final step (step for condensing Y222 and Y491) in Example 2, 2-aminoacetoanilide and Y491 were condensed to give the title compound.
HRMS (FAB-) m/z: [M-H]$^-$ calcd for C$_{25}$H$_{33}$N$_4$O$_7$S$_2$, 565.1791. found, 565.1793

Example 35

4-{[3-(4-dimethylamino-3-furan-2-yl-phenylsulfamoyl)benzenesulfonylamino]methyl}piperidine (Y516)

To a solution (10 ml) of Y244 (332 mg, 0.53 mmol) produced in Example 5 in dichloromethane was added trifluoroacetic acid (3 ml), and the mixture was stirred at room temperature for 20 min. Then, the reaction mixture was concentrated under reduced pressure, and the obtained residue was purified by silica gel column chromatography (eluent; chloroform:methanol (8:1-3:1)) to give the title compound (283 mg, 87%).

$^1$H NMR (500 MHz, CD$_3$OD) δ8.16 (t, 1H, J=1.5 Hz), 8.02 (dd, 2H, J=7.5, 1.5 Hz), 7.72 (t, 1H, J=7.5 Hz), 7.59 (d, 1H, J=1.5 Hz), 7.44 (d, 1H, J=2.5 Hz), 7.32 (d, 1H, J=8.5 Hz), 7.09 (dd, 1H, J=9.0, 2.5 Hz), 6.95 (d, 1H, J=3.0 Hz), 6.55 (dd, 1H, J=3.0, 1.5 Hz), 3.36-3.44 (m, 4H), 2.90 (m, 2H), 2.85 (s, 6H), 2.68 (d, 2H, J=7.0 Hz), 1.85-1.67 (m, 3H), 1.39-1.28 (m, 2H)
$^{13}$C NMR (125 MHz, CD$_3$OD) δ162.6, 151.3, 143.8, 143.3, 142.1, 135.6, 131.9, 131.7, 131.6, 126.5, 126.4, 122.9, 122.2, 121.6, 119.2, 116.9, 113.2, 111.2, 58.3, 45.8, 44.7, 35.4, 27.3, 18.3
HRMS (FAB-) m/z: [M-H]$^-$ calcd for C$_{24}$H$_{29}$N$_4$O$_5$S$_2$, 517.1579. found, 517.1561

Example 36

4-{[3-(4-dimethylamino-3-furan-2-yl-phenylsulfamoyl)benzenesulfonylamino]methyl}-1-butyrylpiperidine (Y639)

To a solution (1.5 ml) of Y516 (60 mg, 0.098 mmol) produced in Example 35 in dimethylformamide were added n-butanoic acid (butyric acid) (20 μl, 0.02 mmol), HBTU (N,N,N',N'-tetramethyl-O— (benzotriazol-1-yl)uronium Hexafluorophosphate) (40 mg, 0.1 mmol) and DIEA (N,N-diisopropylethylamine) (30 ml, 0.18 mmol), and the mixture was stirred at room temperature for 18 hr. Then, the reaction mixture was cooled, poured into cold water, and extracted with chloroform. The obtained chloroform extract was concentrated under reduced pressure, and the residue was purified by silica gel column chromatography (eluent; chloroform:methanol (40:1)) to give the title compound (Y639) (44 mg, 77%).

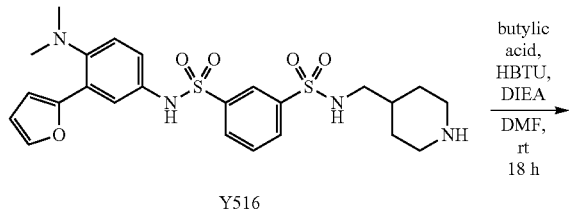

Y516

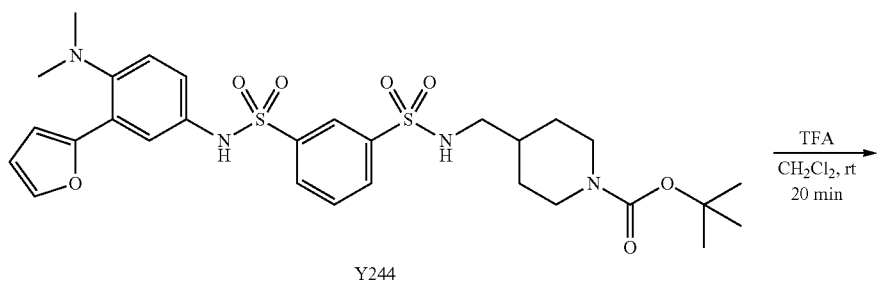

Y244

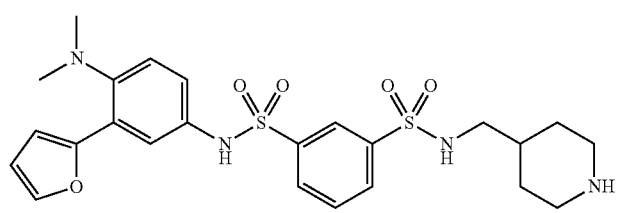

Y516

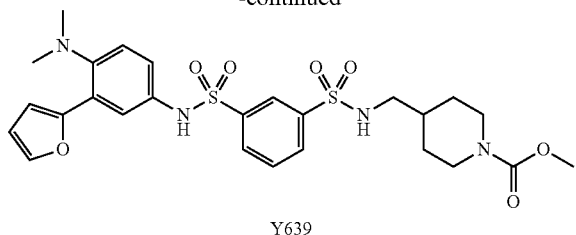

Y639

$^1$H NMR (500 MHz, CDCl$_3$) δ 8.41 (s, 1H), 7.98 (d, 1H, J=8.0 Hz), 7.82 (d, 1H, J=8.0 Hz), 7.52 (t, 1H, J=8.0 Hz), 7.46 (s, 1H), 7.37 (s, 1H), 6.93 (m, 3H), 6.43-6.42 (m, 1H), 5.56 (bs, 1H), 4.55 (d, 1H, J=13.0 Hz), 3.80 (d, 1H, J=13.0 Hz), 2.93-2.86 (m, 1H), 2.74 (t, 2H, J=6.5 Hz), 2.61 (s, 6H), 2.42 (m, 1H), 2.24 (t, 2H, J=7.5 Hz), 1.71-1.62 (m, 3H), 1.56 (q, 2H, J=7.5 Hz), 1.11-0.96 (m, 2H), 0.90 (t, 3H, J=7.5 Hz)

$^{13}$C NMR (125 MHz, CDCl$_3$) δ 171.6, 150.8, 141.4, 140.8, 131.1, 130.8, 129.7, 125.6, 125.2, 122.1, 111.7, 109.5, 76.7, 48.2, 45.4, 43.9, 41.4, 36.4, 35.3, 30.0, 29.1, 18.8, 12.9

HRMS (FAB-) m/z: [M-H]$^+$ calcd for C$_{28}$H$_{37}$N$_4$O$_6$S$_2$, 589.2155. found, 589.2153

The pharmacological test for each compound and the results thereof are explained below.

Experimental Example 1

Evaluation of TGF-β Signal Transduction Inhibitory Activity

The biological activity of a compound was determined by measuring the activation of Smad3/Smad4 complex which is a transcription factor showing activation induced by TGF-β stimulation. That is, a reporter plasmid having a DNA sequence (CAGA sequence), which is activated by binding to Smad3/Smad4 complex, is linked to the upstream of the luciferase gene (luminescence enzyme) was prepared. Mink lung epithelial cells CCL64 (named as x9CAGA/CCL64 cells) stably incorporating this reporter plasmid were established. The x9CAGA/CCL64 cells were cultured in DMEM medium containing 10% FBS, penicillin (100 U/ml), streptomycin (100 g/ml), and blasticidin S (1 μg/ml).

The x9CAGA/CCL64 cells were seeded in a 96 well plate at a concentration of 1.0×10$^4$ cells/well, and cultured in a 5% CO$_2$ incubator at 37° C. The next day, the medium was changed to DMEM medium containing 0.2% FBS, and the test compound was added. The cells were cultured for 1 hr, and then stimulated with 0.5 ng/ml human TGF-β1. After culture for 16 hr, the cells were washed with PBS, and lysed with 30 μl of cell lysis solution. To 20 μl thereof was added 30 μl of substrate solution containing luciferin, adenosine triphosphate, coenzyme A and magnesium ion, and the amount of luminescence produced by the enzyme reaction with luciferase was measured. The luminescence level of each well was measured using a Packard EnVision plate reader.

The TGF-β signal transduction inhibitory activity of each compound in the x9CAGA/CCL64 cells was calculated from the ratio of the measurement values of the test compound-free well and the well with addition. The results are shown in the following Tables.

TABLE 1

| KUSC- | Ex. | structure | inhibitory activity (%) |
|---|---|---|---|
| Y043 | 7 | (structure) | 67%[a] |
| Y053 | 8 | (structure) | 67%[a] |
| Y191 | 9 | (structure) | 54%[b] |

TABLE 1-continued

| KUSC- | Ex. | Structure | inhibitory activity (%) |
|---|---|---|---|
| Y205 | 10 | 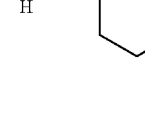 | 60%[b] |
| Y335 | 1 | 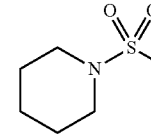 | [c] |

In Table 1, a) shows the inhibitory activity with 50 μM test compound, b) shows the inhibitory activity with 20 μM test compound, and c) shows $IC_{50}$ of 0.8 μM.

TABLE 2

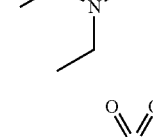

| KUSC- | Ex. | $R_{13a}$ | inhibitory activity (%) |
|---|---|---|---|
| Y029 | 11 | 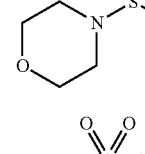 | 88%[a] |
| Y080 | 12 | | 66%[a] |
| Y081 | 13 | | 45%[a] |
| Y082 | 14 | | 29%[a] |
| Y083 | 15 | H | 24%[a] |
| Y101 | 16 | 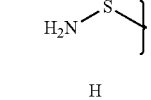 | 74%[a] |

In Table 2, a) shows the inhibitory activity with 50 μM test compound.

TABLE 3

| KUSC- | Ex. | $R_{13b}$ | $R_{13c}$ | $R_{13d}$ | $IC_{50}$ (μM) |
|---|---|---|---|---|---|
| Y098 | 17 | H | H | H | 27 |
| Y141 | 18 | $OCH_3$ | H | H | 17 |
| Y142 | 19 | H | $OCH_3$ | H | 22 |
| Y140 | 20 | H | H | $OCH_3$ | 30 |
| Y145 | 33 | $CF_3$ | H | H | 8.0 |
| Y147 | 34 | H | H | NHAc | 18 |
| Y155 | 21 | $CH_3$ | H | H | 14 |

Ac: $C(O)-CH_3$

TABLE 4

| KUSC- | Ex. | R₁₃ | R₁₂ | IC₅₀ (μM) |
|---|---|---|---|---|
| Y177 | 22 | tert-butyl | H | 2.0 |
| Y224 | 2 | piperidinyl | H | 2.4 |
| Y186 | 4 | diethylamino | H | 3.6 |
| Y178 | 23 | dimethylamino | H | 15 |
| Y185 | 3 | morpholinyl | H | 24 |
| Y192 | 24 | acetyl | H | (>18.4%) |
| Y195 | 25 | CH(OH)CH₃ | H | (>12.2%) |
| Y196 | 26 | OH | H | 16 |
| Y198 | 32 | glycidyl ether | H | (>30.0%) |
| Y241 | 27 | N₃ | H | 0.7 |
| Y260 | 28 | Boc-piperazinyl | H | 1.5 |
| Y366 | 31 | phenacyl | H | 7.3 |

In Table 4, the inhibitory activity of Y192, Y195 and Y198 with 20 μM test compound is shown.

TABLE 5

| KUSC- | Ex. | R₁₃ | R₁₂ | IC₅₀ (μM) |
|---|---|---|---|---|
| Y244 | 5 | dimethylamino | furan-2-yl | 0.6 |
| Y250 | 6 | piperidinyl | furan-2-yl | 2.5 |
| Y284 | 29 | H | furan-2-yl | 6.7 |
| Y296 | 30 | H | thiophen-2-yl | 4.6 |

As is clear from Tables 1-5, the compound of the present invention was shown to have a TGF-β signal transduction inhibitory activity.

Experimental Example 2

Evaluation of TGF-β Signal Transduction Inhibitory Activity

The same test as in Experimental Example 1 was performed for Y516 and Y639, and the TGF-β signal transduction inhibitory activity was calculated. The IC50 values of the TGF-β signal transduction inhibitory activity of Y516 were 66 μM and 3.9 μM, respectively.

Experimental Example 3

Evaluation of TGF-β-Induced Epithelial-Mesenchymal Transition (EMT) Inhibitory Activity Human retinal pigment epithelial cells (ARPE-19 cells) were seeded in a 96 well plate at a concentration of $1.2 \times 10^4$ cells/well, and cultured overnight (5% $CO_2$, 37° C.) in DMEM/F12 medium containing 10% fetal bovine serum, penicillin (100 U/mL), streptomycin (100 μg/mL) and Hepes (10 mM). The next day, the medium was changed to a serum-free medium, and a test compound was added. After 1 hr, the cells were stimulated with human TGF-β2 (10 ng/mL) and human TNF (10 ng/mL). After culture for 2 days, the cells were stained with Giemsa, and the influence of the compound on the formation of cell aggregates was evaluated.

As a result, Y244 remarkably suppressed EMT induced by TGF-β (FIG. 1). SB4831542 (TGF-β receptor kinase inhibitor) was used as a positive control.

Experimental Example 4

Evaluation of Influence on Activation of Liver Kupffer Cells in Primary Culture System Wistar rat (bred under SPF, male, 15-week-old) was subjected to laparotomy under pentobarbital anesthesia, a catheter was inserted into the portal vein, and perfusion was performed successively with a washing solution for hemorrhage, a 0.06% pronase solution (manufactured by Carbiochem), and a 0.03% collagenase (manufactured by Wako Pure Chemical Industries, Ltd.) solution. Then, the liver was isolated and incubated in a liver Kupffer cell separation buffer containing 0.057% pronase and 0.057% collagenase, and supplemented with 2 mg/mL DNaseI (1 mL, manufactured by Roche Diagnostics) in a warm bath at 36° C. for 30 min. During this period, the pH of the lysate was maintained at 7.2-7.4 with 1N NaOH. Then, the hepatic tissue digestive product was filtered through a mesh, a liver Kupffer cell separation buffer was added to the obtained filtrate to the total amount of 150 mL. The mixture was dispensed to three 50-mL polypropylene tubes, and centrifuged at 4° C., 2000 rpm for 8 min. The supernatant in the polypropylene tubes was removed by suction, DNaseI solution was added to each tube by 0.2 mL, Gey's Balanced Salt Solution was added and blended by pipetting to the total amount of 100 mL. The mixture was dispensed again to two 50 mL-polypropylene tubes, and centrifuged at 4° C., 2000 rpm for 8 min. The supernatant in the polypropylene tubes was removed by suction, 0.2 mL of DNaseI solution was added to each tube, Gey's Balanced Salt Solution was added and blended by pipetting to the total amount of 67.5 mL. The mixture was transferred into a beaker, and mixed with Nycodenz (manufactured by SIGMA) solution (final concentration 7.75%) (27 mL) sterilized by filtration with 0.22 μm filter. The cell suspension was dispensed to eight 15 mL-tubes, 1 mL of Gey's Balanced Salt Solution was layered thereon, and centrifuged at 4° C., 3200 rpm for 15 min to separate the liver Kupffer cells. The separated liver Kupffer cells were suspended in DMEM medium containing 10% fetal bovine serum (manufactured by EQUITECH-BIO) and 1% preservative (manufactured by Invitrogen) at a concentration of $1 \times 10^5$ cells/mL, seeded by 3 mL in a 6 cm-diameter cell culture dish (manufactured by CORNING), and cultured overnight at 37° C., 5% $CO_2$. The next day, the medium was changed as well as a test compound was simultaneously added, and the cells were cultured for 7 days while changing the medium (±test compound) every 24 hr. Along therewith, the cells treated with 0.1% ethanol (solvent) as a control, and the cells treated with SB431542, which is a TGF-β receptor inhibitor as a positive control were also prepared and cultured in the same manner for 7 days. The morphological changes in the bright field were observed 7 days later.

On the other hand, respective cells were washed with phosphate buffer (PBS: phosphate buffered saline) 7 days later, and fixed with 4% para-formaldehyde at room temperature for 10 min. Thereafter, the cells were washed with PBS containing 0.05% Tween 20 (PBST), and blocked with PBST containing 5% skim milk at room temperature for 30 min. The cells were washed with PBST, treated with a solution wherein Cy3-labeled anti-αSMA antibody was diluted 1/200 with PBST containing 5% skim milk, and left standing at 4° C. overnight. Then, the cells were washed with PBST, and the α smooth muscle actin (αSMA) expression level was observed under a fluorescence microscope.

Figure 2:
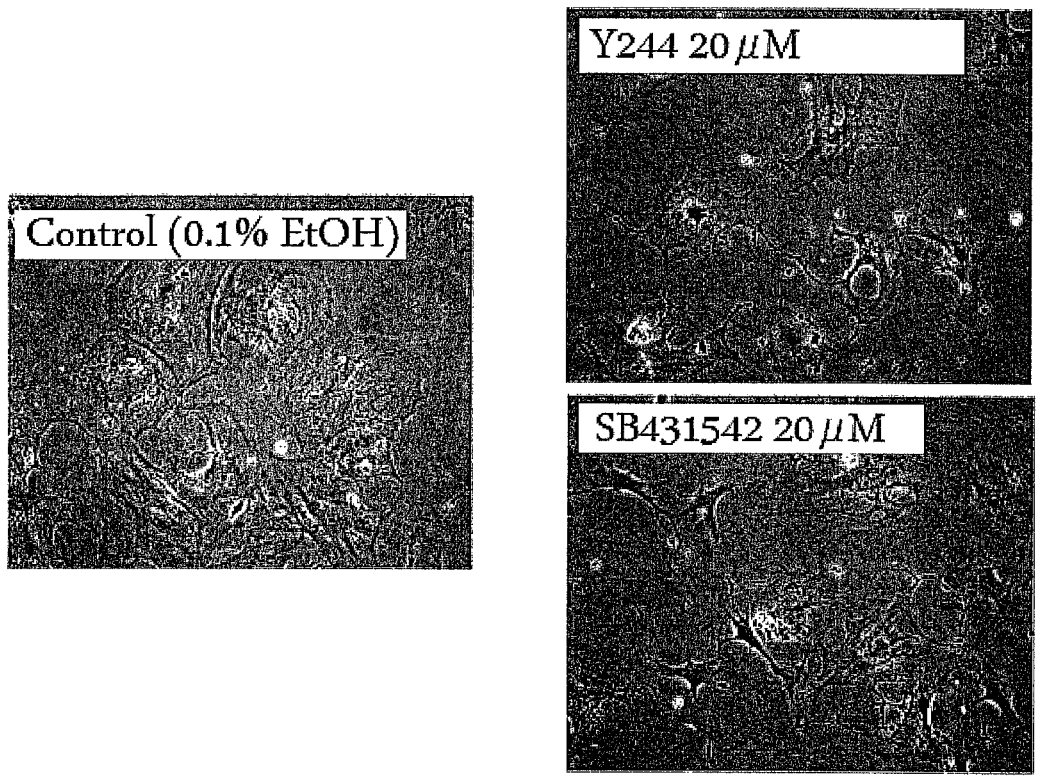
FIG. 2 shows the effect of Y244 on the cell morphological
changes caused by the activation of liver Kupffer cell.
Figure 3:
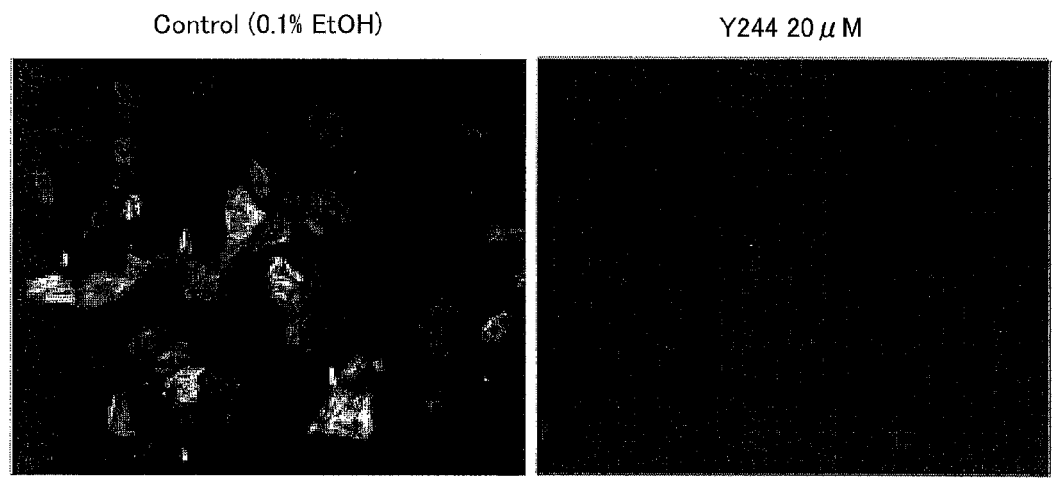
FIG. 3 shows the effect of Y244 on the expression of a
smooth muscle actin caused by the activation of liver Kupffer
cell.

The cell morphology in the bright field after 7 days of culture is shown in FIG. 2. In the primary culture system, Y244 suppressed cell morphology change caused by the activation of liver Kupffer cells. As shown in FIG. 3, in the primary culture system, Y244 remarkably suppressed the expression of a smooth muscle actin associated with the activation of liver Kupffer cells.

Experimental Example 4

Examination of Anti-Fibrillization Action Using Mouse Bile Duct Ligation Induced Hepatic Fibrosis Model (BDL Model: Bile Duct Ligation Model)

Hepatopathy caused by accumulation of bile in the liver and therewith associated liver fibrillization are induced by ligating the bile duct of mouse. The effect of the test compound on the hepatopathy and liver fibrillization associated therewith was evaluated.

(Surgery)

ICR mice (male, 8-week-old) after 1 week of acclimation were divided into 6 groups based on the body weight (10 per each group (6 only in sham treatment group), and subjected to bile duct ligation operation by the following steps. Under isoflurane inhalation anesthesia, the abdomen hair of the animal was shaved, the operation field was disinfected with povidoneiodo and rubbing 70% ethanol solution, the abdomen skin and the muscle layer were incised, the intrahepatic bile duct hepatic portal region was confirmed by visual observation, and the common bile duct was detached and exposed. The portion of conjugation of bile canaliculi (common bile duct), and an about 5 mm downstream thereof were each ligated with a suture thread to block the bile flow path. The center of the two ligated portions was cut with micro scissors to confirm absence of bile leakage, and saline (0.3 ml) was added dropwise into the abdominal cavity. The abdomen muscle layer was continuously sutured with a suture thread, after which the abdomen skin was sutured. In the sham operation, only the detachment of the common bile duct was performed.

(Breeding and Observation)

The animals after operation were checked once per day for general condition, and the animals with abnormality were euthanized and removed from the experiment. The animals used for the experiment were bred in a facility set to 24±2° C., humidity 50±10%, lighting hours 12 hr (7-19:00), and allowed free-feeding of radiation-sterilized solid feed (Nosan Corporation) and water having water quality meeting the Waterworks Law.

(Compound Administration)

Y244 and Y516 were administered once a day for 14 days from the day of operation. That is, 2, 0.2 or 0.02 mg/ml administration solution was prepared when in use by diluting a stock solution of 100 mg/ml compound, which was prepared with 100% ethanol, with sterilized saline (final concentration of ethanol was uniformly 2%), and administered to the animal at 5 ml/kg from the tail vein. Simultaneously, saline containing 2% ethanol (solvent) was administered to the sham treatment animal and solvent administration animal.
(Tissue Collection)

Hepatic tissues were collected as shown below on day 14 post-operation. After fasting for about 16 hr from the previous day, the whole blood was collected from the caudal vena cava under isoflurane inhalation anesthesia to allow death from exsanguination, the liver was isolated, and the lateral left lobe was separated. The center portion was collected in about 2 mm thickness for mRNA extraction, and preserved in RNALater (Ambion) at 4° C.
(Examination of Gene Expression in Hepatic Tissue)

mRNA was extracted from the hepatic tissue preserved in RNALater by using an RNA purification kit RNeasy Micro Kit (manufactured by QIAGEN), and the RNA concentration was determined using a spectrophotometer (Nano Drop). Using this mRNA as a template, RT reaction was performed according to the package insert by using a PrimeScript™ RT reagent Kit (manufactured by TAKARA). Using SYBR® Premix EX Taq™ (manufactured by TAKARA), a reaction mixture was prepared according to the package insert, qPCR reaction was performed using respective primers for αSMA and the internal standard GAPDH (manufactured by Invitrogen), and the mRNA expression level was quantified.
(Results)

Figure 4:
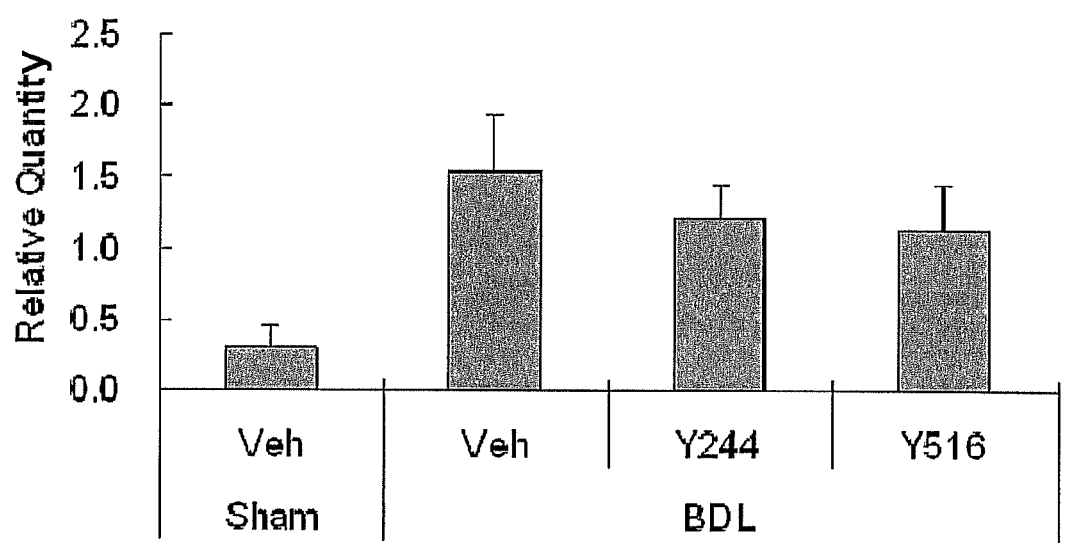
FIG. 4 shows the effects of Y244 and Y516 on the mRNA
expression of a smooth muscle actin in the liver tissue, which
is caused by the liver fibrillization.

The results are shown in FIG. 4. Y244 and Y516 significantly suppressed mRNA expression level of a smooth muscle actin in the liver tissue, which is associated with liver fibrillization, in the mouse bile duct ligation induced hepatic fibrosis model.

The above results suggest that the compound of the present invention is useful as a therapeutic and/or prophylactic agent for TGF-β-related diseases such as sclerotic disease, cancer and the like, which are associated with fibrillization.

INDUSTRIAL APPLICABILITY

Since the compound of the present invention effectively inhibits TGF-β signal transduction, it is useful as a prophylactic or therapeutic drug for TGF-β-related diseases.

This application is based on patent application No. 2010-032810 filed in Japan (filing date: Feb. 17, 2010), the contents of which are encompassed in full herein.

The invention claimed is:
1. A compound represented by the following formula (I):

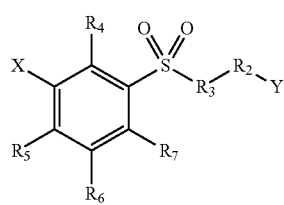

wherein
Y is a hydrogen atom, a carboxyl group or

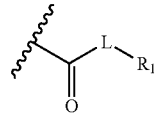

wherein
L is an oxygen atom or a bond, and $R_1$ is optionally substituted $C_{1-6}$ alkyl;

$R_2$ is

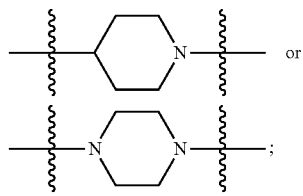

$R_3$ is —$NR_8$—$R_9$— or a bond, wherein $R_8$ is a hydrogen atom or $C_{1-6}$ alkyl, and $R_9$ is $C_{1-6}$ alkylene;
$R_4$, $R_5$, $R_6$ and $R_7$ are the same or different and each is a hydrogen atom or $C_{1-6}$ alkyl; and
X is

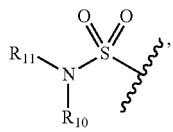

wherein $R_{10}$ is a hydrogen atom or $C_{1-6}$ alkyl; and
$R_{11}$ is optionally substituted phenyl, optionally substituted $C_{1-6}$ alkyl or a hydrogen atom, or
$R_{10}$ and $R_{11}$ form, together with the nitrogen atom bonded thereto, an optionally substituted 5- to 7-membered cyclic amino group,
or a physiologically acceptable salt thereof.

2. The compound or a physiologically acceptable salt thereof according to claim 1, wherein Y is

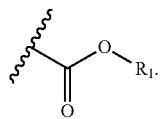

3. The compound or a physiologically acceptable salt thereof according to claim 1, wherein $R_{11}$ is a group represented by the following formula:

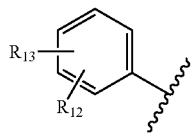

wherein
$R_{12}$ is a hydrogen atom, furyl or thienyl; and
$R_{13}$ is optionally substituted amino, optionally substituted $C_{1-6}$ alkyl, hydroxy, optionally substituted $C_{1-6}$ alkoxy, $C_{1-6}$ alkanoyl, $C_{6-10}$ aroyl or $N_3$.

4. The compound or a physiologically acceptable salt thereof according to claim 3, wherein $R_{13}$ is an amino group optionally mono- or di-substituted by $C_{1-6}$ alkyl or $C_{1-6}$ alkanoyl, or an optionally substituted 5- to 7-membered cyclic amino group.

5. A compound which is
4-[3-(piperidine-1-sulfonyl)benzenesulfonyl]piperazine-1-carboxylic acid tert-butyl ester, 4-{[3-(piperidine-1-sulfonyl)benzenesulfonylamino]-methyl}-piperidine-1-carboxylic acid benzyl ester,
4-({methyl-[3-(methyl-p-tolylsulfamoyl)benzenesulfonyl]amino}methyl)piperidine-1-carboxylic acid tert-butyl ester,
4-[({3-[(4-tort-butylphenyl)methylsulfamoyl]benzenesulfonyl}methylamino)-methyl]piperidine-1-carboxylic acid tert-butyl ester,
4-{[3-(4-tert-butylphenylsulfamoyl)-2,4,5,6-tetramethylbenzenesulfonylamino]methyl}piperidine-1-carboxylic acid tert-butyl ester,
4-{[3-(piperidine-1-sulfonyl)benzenesulfonylamino]methyl}piperidine-1-carboxylic acid tert-butyl ester,
4-[(3-diethylsulfamoylbenzenesulfonylamino)methyl]piperidine-1-carboxylic acid tert-butyl ester,
4-{[3-(morpholine-4-sulfonyl)benzenesulfonylamino]methyl}piperidine-1-carboxylic acid tert-butyl ester,
4-[(3-sulfamoylbenzenesulfonylamino)methyl]piperidine-1-carboxylic acid tert-butyl ester,
4-(benzenesulfonylaminomethyl)piperidine-1-carboxylic acid tert-butyl ester,
4-{[3-(cyclohexylmethylsulfamoyl)benzenesulfonylamino]methyl}piperidine-1-carboxylic acid tert-butyl ester,
4-[(3-phenylsulfamoylbenzenesulfonylamino)methyl]piperidine-1-carboxylic acid tert-butyl ester,
4-{[3-(4-methoxyphenylsulfamoyl)benzenesulfonylamino]methyl}piperidine-1-carboxylic acid tert-butyl ester,
4-{[3-(3-methoxyphenylsulfamoyl)benzenesulfonylamino]methyl}piperidine-1-carboxylic acid tert-butyl ester,
4-{[3-(2-methoxyphenylsulfamoyl)benzenesulfonylamino]methyl}piperidine-1-carboxylic acid tert-butyl ester,
4-{[3-(4-trifluoromethylphenylsulfamoyl)benzenesulfonylamino]methyl}piperidine-1-carboxylic acid tert-butyl ester,
4-{[3-(2-acetylaminophenylsulfamoyl)benzenesulfonylamino]methyl}piperidine-1-carboxylic acid tert-butyl ester,
4-[(3-p-tolylsulfamoylbenzenesulfonylamino)methyl]piperidine-1-carboxylic acid tert-butyl ester,
4-{[3-(4-tert-butylphenylsulfamoyl)benzenesulfonylamino]methyl}piperidine-1-carboxylic acid tert-butyl ester,
4-{[3-(4-piperidin-1-yl-phenylsulfamoyl)benzenesulfonylamino]methyl}piperidine-1-carboxylic acid tert-butyl ester,
4-{[3-(4-diethylaminophenylsulfamoyl)benzenesulfonylamino]methyl}piperidine-1-carboxylic acid tert-butyl ester,
4-{[3-(4-dimethylaminophenylsulfamoyl)benzenesulfonylamino]methyl}piperidine-1-carboxylic acid tert-butyl ester,
4-{[3-(4-morpholin-4-yl-phenylsulfamoyl)benzenesulfonylamino]methyl}piperidine-1-carboxylic acid tert-butyl ester,
4-{[3-(4-acetylphenylsulfamoyl)benzenesulfonylamino]methyl}piperidine-1-carboxylic acid tert-butyl ester,
4-({3-[4-(1-hydroxyethyl)phenylsulfamoyl]benzenesulfonylamino}methyl)piperidine-1-carboxylic acid tert-butyl ester,
4-{[3-(4-hydroxyphenylsulfamoyl)benzenesulfonylamino]methyl}piperidine-1-carboxylicacid tert-butyl ester,
4-{[3-(4-oxanylmethoxyphenylsulfamoyl)benzenesulfonylamino]methyl}piperidine-1-carboxylic acid tert-butyl ester,
4-{[3-(4-azidophenylsulfamoyl)benzenesulfonylamino]methyl}piperidine-1-carboxylic acid tert-butyl ester,
4-(4-{3-[(1-tert-butoxycarbonylpiperidin-4-ylmethyl)sulfamoyl]benzenesulfonylamino}phenyl)piperazine-1-carboxylic acid tert-butyl ester,
4-({3-[4-(4-benzoylpiperazin-1-yl)phenylsulfamoyl]benzenesulfonylamino}methyl)piperidine-1-carboxylic acid tert-butyl ester,
4-{[3-(4-dimethylamino-3-furan-2-yl-phenylsulfamoyl)benzenesulfonylamino]methyl}piperidine-1-carboxylic acid tert-butyl ester,
4-{[3-(3-furan-2-yl-4-piperidin-1-yl-phenylsulfamoyl)benzenesulfonylamino]methyl}piperidine-1-carboxylic acid tert-butyl ester,
4-{[3-(3-furan-2-yl-phenylsulfamoyl)benzenesulfonylamino]methyl}piperidine-1-carboxylic acid tert-butyl ester,
4-{[3-(3-thiophen-2-yl-phenylsulfamoyl)benzenesulfonylamino]methyl}piperidine-1-carboxylic acid tert-butyl ester,
or a physiologically acceptable salt thereof.

6. The compound or a physiologically acceptable salt thereof according to claim 1, which is 4-{[3-(4-dimethylamino-3-furan-2-yl-phenylsulfamoyl)benzenesulfonylamino]methyl}piperidine, 4-{[3-(4-dimethylamino-3-furan-2-yl-phenylsulfamoyl)benzenesulfonylamino]methyl}-1-butyryl-piperidine or a physiologically acceptable salt thereof.

7. A pharmaceutical composition comprising the compound or a physiologically acceptable salt thereof according to claim 1.

8. A method for treatment of tissue fibrillization induced by TGF-β in a sclerotic disease or cancer in a mammal, comprising administering a therapeutically effective amount of the compound or a physiologically acceptable salt thereof according to claim 1 to said mammal.

9. A method for treatment of tissue fibrillization induced by TGF-β in a sclerotic disease or cancer in a mammal, comprising administering a therapeutically effective amount of the compound or a physiologically acceptable salt thereof according to claim 2 to said mammal.

10. A method for treatment of tissue fibrillization induced by TGF-β in a sclerotic disease or cancer in a mammal, comprising administering a therapeutically effective amount of the compound or a physiologically acceptable salt thereof according to claim 3 to said mammal.

11. A method for treatment of tissue fibrillization induced by TGF-β in a sclerotic disease or cancer in a mammal, comprising administering a therapeutically effective amount of the compound or a physiologically acceptable salt thereof according to claim 4 to said mammal.

12. A method for treatment of tissue fibrillization induced by TGF-β in a sclerotic disease or cancer in a mammal, comprising administering a therapeutically effective amount of the compound or a physiologically acceptable salt thereof according to claim 5 to said mammal.

13. A method for treatment of tissue fibrillization induced by TGF-β in a sclerotic disease or cancer in a mammal, comprising administering a therapeutically effective amount of the compound or a physiologically acceptable salt thereof according to claim 6 to said mammal.

14. A pharmaceutical composition comprising the compound or a physiologically acceptable salt thereof according to claim 2.

15. A pharmaceutical composition comprising the compound or a physiologically acceptable salt thereof according to claim 3.

16. A pharmaceutical composition comprising the compound or a physiologically acceptable salt thereof according to claim 4.

17. A pharmaceutical composition comprising the compound or a physiologically acceptable salt thereof according to claim 5.

18. A pharmaceutical composition comprising the compound or a physiologically acceptable salt thereof according to claim 6.

\* \* \* \* \*